(12) United States Patent
Ishikawa et al.

(10) Patent No.: US 11,142,497 B2
(45) Date of Patent: Oct. 12, 2021

(54) PLANT GROWTH INHIBITING AGENT, AND PLANT GROWTH INHIBITING METHOD USING SAME

(71) Applicants: NATIONAL UNIVERSITY CORPORATION KUMAMOTO UNIVERSITY, Kumamoto (JP); Nippon Soda Co., Ltd., Tokyo (JP)

(72) Inventors: Hayato Ishikawa, Kumamoto (JP); Tokio Tani, Kumamoto (JP); Shinichiro Sawa, Kumamoto (JP); Takashi Ishida, Kumamoto (JP); Yusuke Fukushima, Kanagawa (JP); Jun Inagaki, Kanagawa (JP)

(73) Assignees: National University Corporation Kumamoto University, Kumamoto (JP); Nippon Soda Co., Ltd., Tokyo (JP)

( * ) Notice: Subject to any disclaimer, the term of this patent is extended or adjusted under 35 U.S.C. 154(b) by 233 days.

(21) Appl. No.: 16/482,790

(22) PCT Filed: Feb. 6, 2018

(86) PCT No.: PCT/JP2018/004094
§ 371 (c)(1),
(2) Date: Aug. 1, 2019

(87) PCT Pub. No.: WO2018/147292
PCT Pub. Date: Aug. 16, 2018

(65) Prior Publication Data
US 2021/0276950 A1   Sep. 9, 2021

(30) Foreign Application Priority Data
Feb. 7, 2017   (JP) .............................. JP2017-020616

(51) Int. Cl.
*C07D 207/46*   (2006.01)
*A01N 43/36*   (2006.01)

(52) U.S. Cl.
CPC ........... *C07D 207/46* (2013.01); *A01N 43/36* (2013.01)

(58) Field of Classification Search
CPC .............................. C07D 207/46; A01N 43/36
See application file for complete search history.

(56) References Cited

U.S. PATENT DOCUMENTS

| | | | |
|---|---|---|---|
| 5,102,904 A | 4/1992 | Kameswaran | |
| 5,472,933 A | 12/1995 | Zimmerman et al. | |
| 6,391,827 B1 | 5/2002 | Meazza et al. | |

FOREIGN PATENT DOCUMENTS

| | | |
|---|---|---|
| CA | 2075586 A1 | 2/1993 |
| JP | 03-251561 A | 11/1991 |
| JP | 05-320144 A | 12/1993 |
| JP | 2001-026577 A | 1/2001 |
| JP | 2008-007455 A | 1/2008 |
| JP | 2013-253052 A | 12/2013 |
| JP | 2014-094909 A | 5/2014 |
| WO | WO 2015/039073 A1 | 3/2015 |

OTHER PUBLICATIONS

Budzianowski et al., "Caffeoylmalic and two pyrrole acids from *Parietaria Officinalis*," Phytochemistry, 1990, 29(10):3299-3301.
Cai et al., "Manipulation of Regulatory Genes Reveals Complexity and Fidelity in Hormaomycin Biosynthesis," Chemistry & Biology, Jun. 20, 2013, 20(6):839-846.
Choi et al., "Chemistry of 1-Methoxypyrrole-2-carboxylic Acid," Bull. Korean Chem. Soc., 1989, 10(6):547-551.
Hino et al. "FK409, a novel vasodilator isolated from the acid-treated fermentation broth of *Streptomyces griseosporeus*," The Journal of Antibiotics, Nov. 1989, 42(11):1584-1588.
Ishikawa, Yuto, "Development of N-alkoxy pyrrole as agricultural pesticides," Kumamoto University, New Technology Presentation Meetings, online Aug. 1, 2017, search date Apr. 11, 2018, URL:https://shingi.ist.go.jp/var.rev1/0000/1814/2017_kumamoto-u_3.pdf.
Sugiyama et al., "Surugapyrroles A and B, Two New N-Hydroxypyrroles, as DPPH Radical-Scavengers from *Streptomyces* sp. USF-6280 Strain," Bioscience, Biotechnology, and Biochemistry, 2009, 73(1):230-232.
Yoshimura et al., "Novel N-Oxypyrrole Derivatives from *Streptomyces werraensis*; Isolation, Synthesis and Plant Growth Inhibitory Activity," The Chemical Society of Japan Spring Annual Meeting, Abstracts, vol. 97, Mar. 3, 2017, 1C6-12.
(Continued)

*Primary Examiner* — Kamal A Saeed
(74) *Attorney, Agent, or Firm* — Foley & Lardner LLP

(57) ABSTRACT

An object of the present invention is to provide a novel plant growth inhibiting agent and a plant growth inhibiting method using the same. The plant growth inhibiting agent of the present invention comprises, as an active ingredient, a compound represented by the following formula (I') and/or a salt thereof. In the formula (I'), $R^{1a}$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, or the like; $R^2$ represents a substituted or unsubstituted $C_1$ to $C_{20}$ alkylene group, a substituted or unsubstituted $C_6$ to $C_{14}$ arylene group, or the like; $R^{3a}$ represents OH, a substituted or unsubstituted $C_1$ to $C_6$ alkoxy group, or the like; X represents an oxygen atom; Y represents a substituent; q represents any integer of 0 to 3; n represents 0 or 1; and m represents 0 or 1.

(I')

$(Y)_q \overset{\displaystyle \diagup\!\!\!\diagdown}{\underset{\underset{\displaystyle O-[R^2]_n-[X]_m-R^{1a}}{N}}{}} COR^{3a}$

8 Claims, 13 Drawing Sheets

(56) References Cited

OTHER PUBLICATIONS

Zlatopolskiy et al., "Convergent Syntheses of N-Boc-Protected (2S,4R)-4-(Z)-Propenylproline and 5-Chloro-1-(methoxymethoxy)pyrrol-2-carboxylic Acid—Two Essential Building Blocks for the Signal Metabolite Hormaomycin," Eur. J. Org. Chem., Nov. 2004, 2004(21):4492-4502.

[Fig. 1]
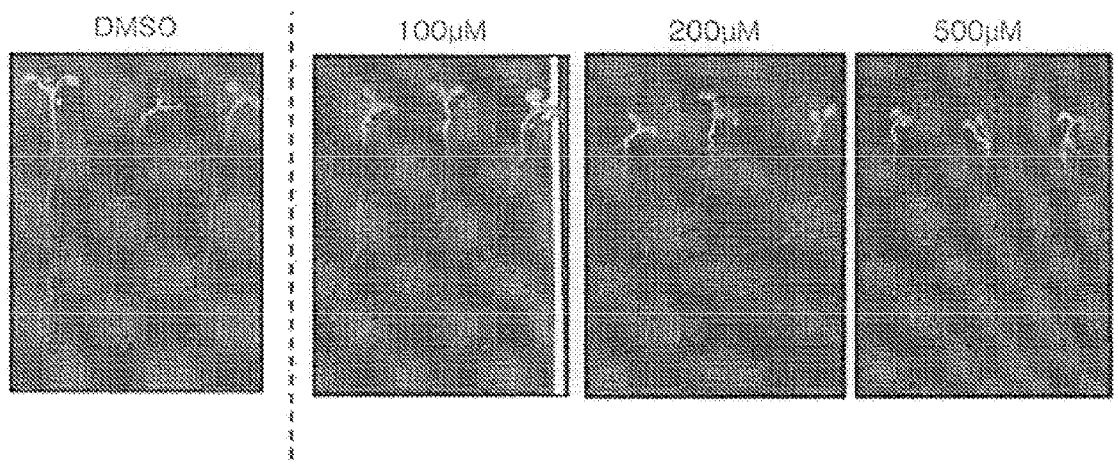
[Fig. 2]
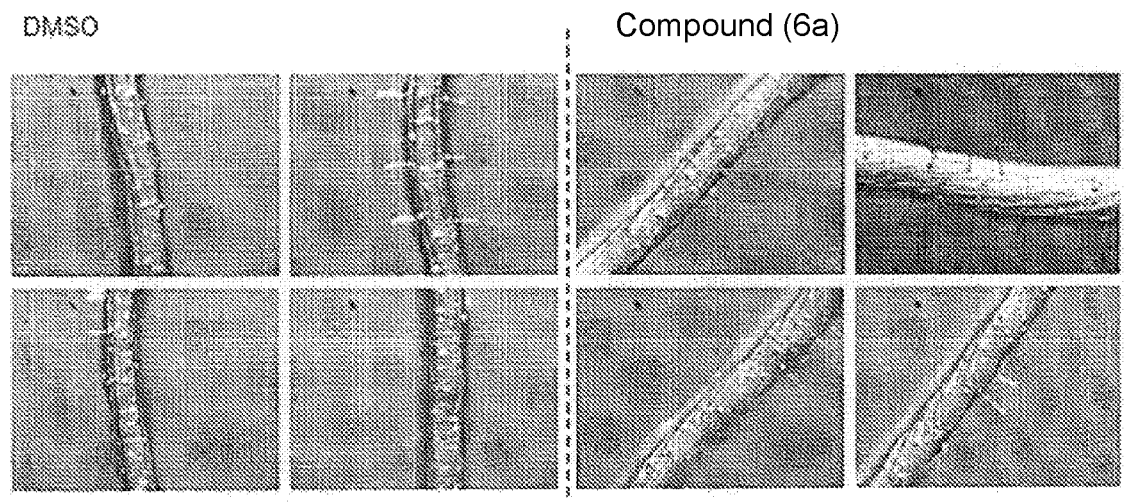

[Fig. 3]
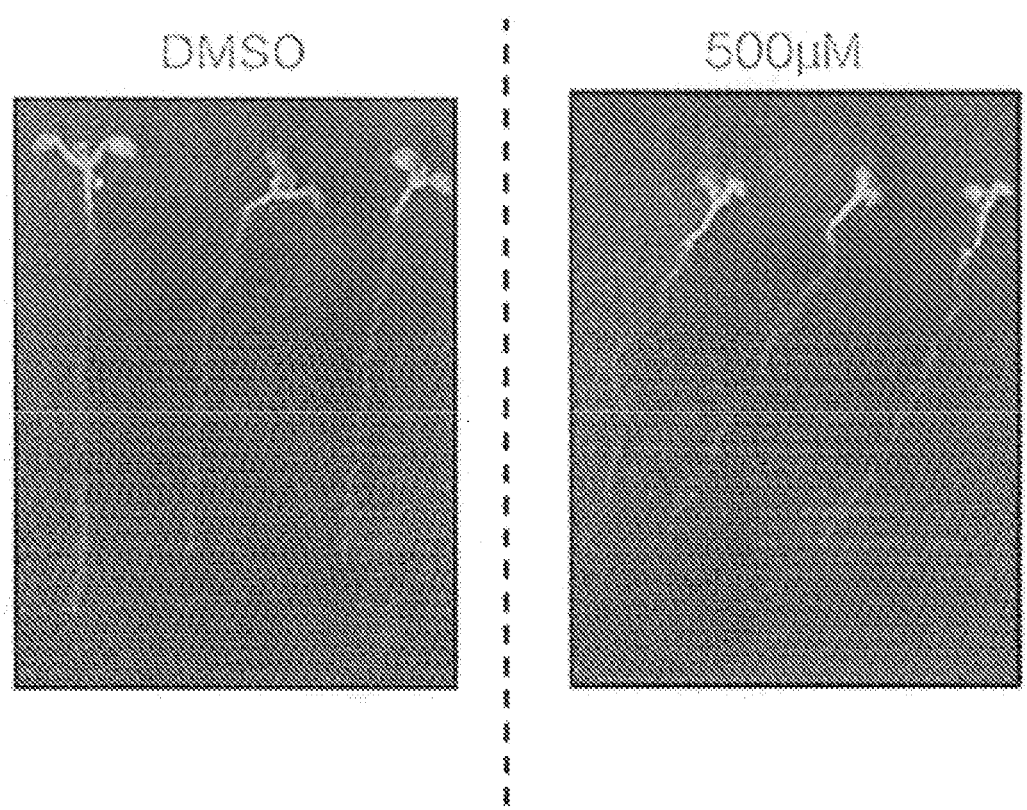

[Fig. 4]
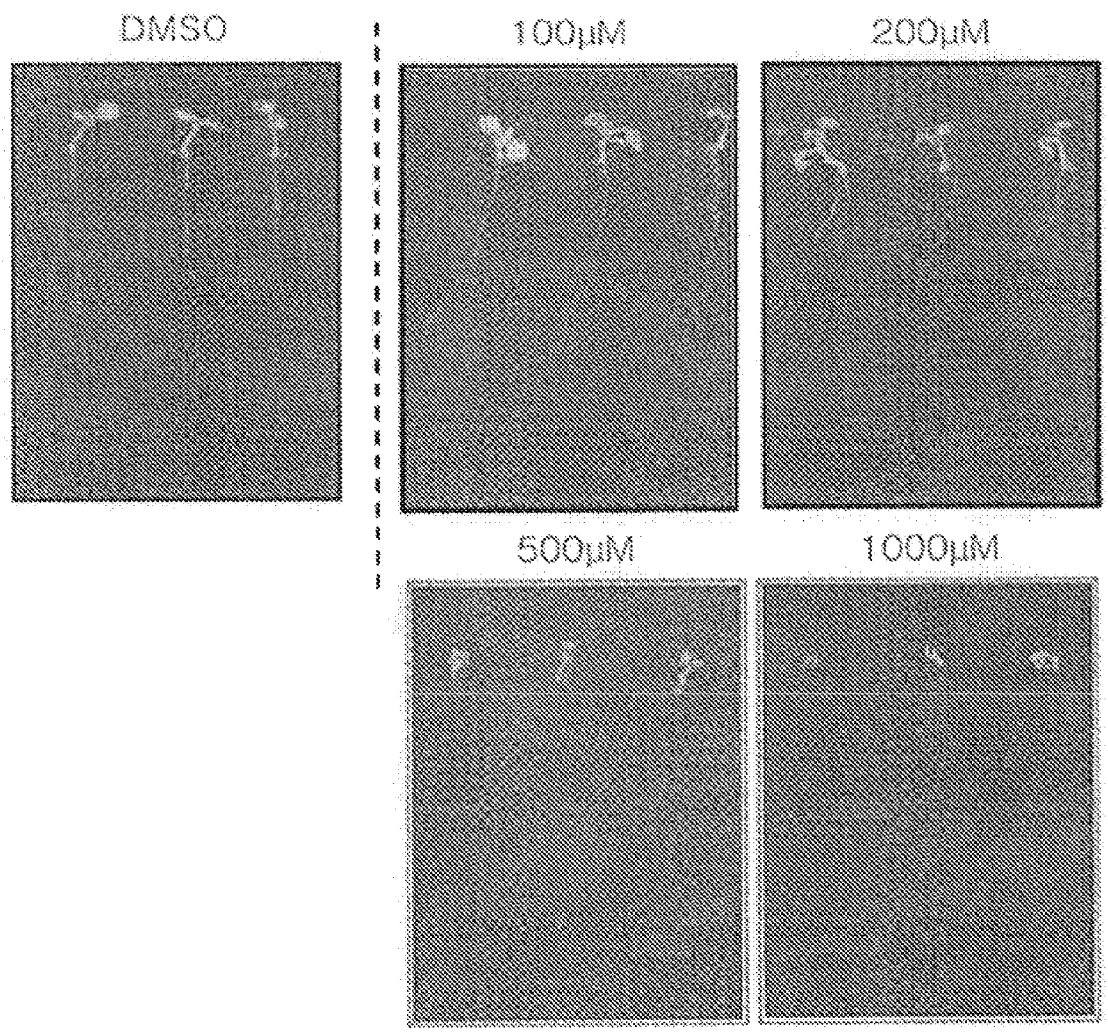

[Fig. 5]
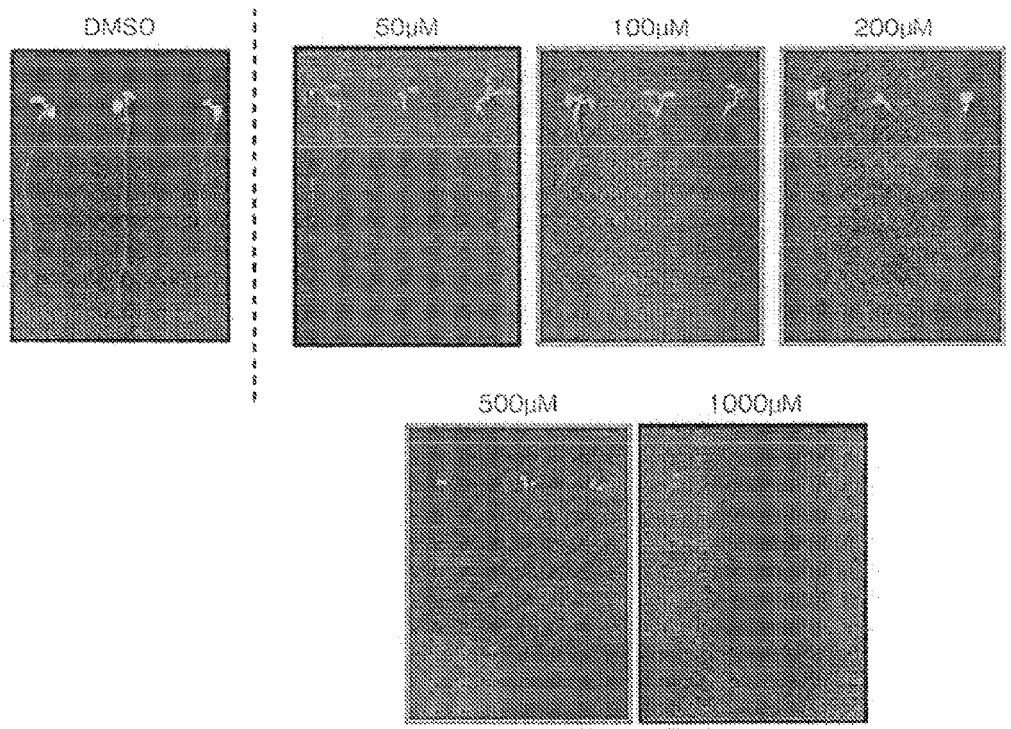
[Fig. 6]
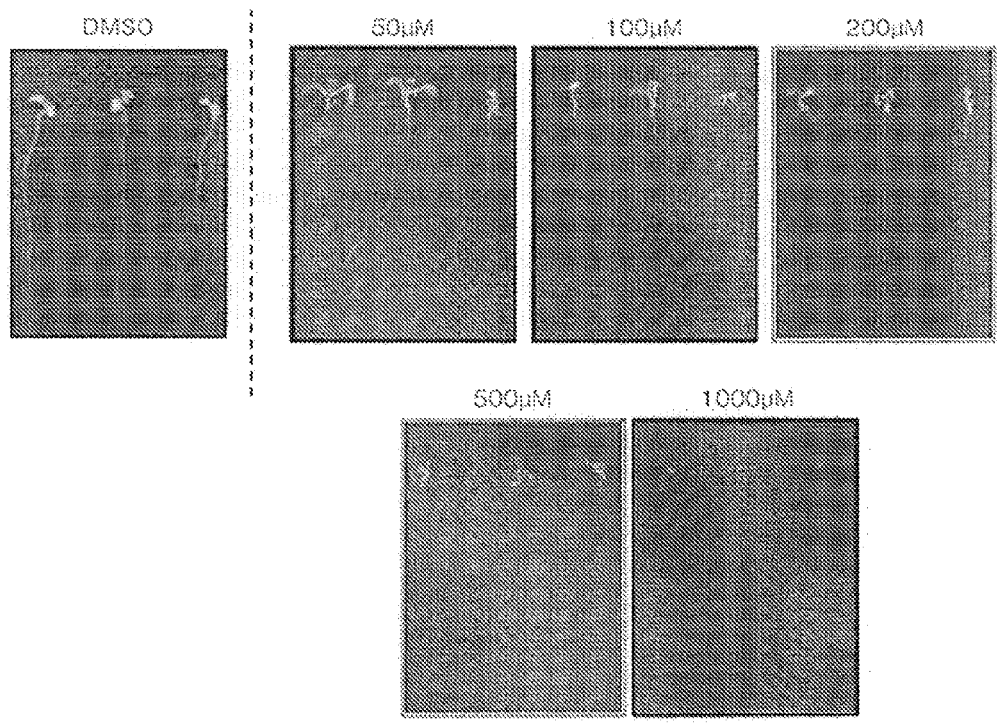

[Fig. 7]
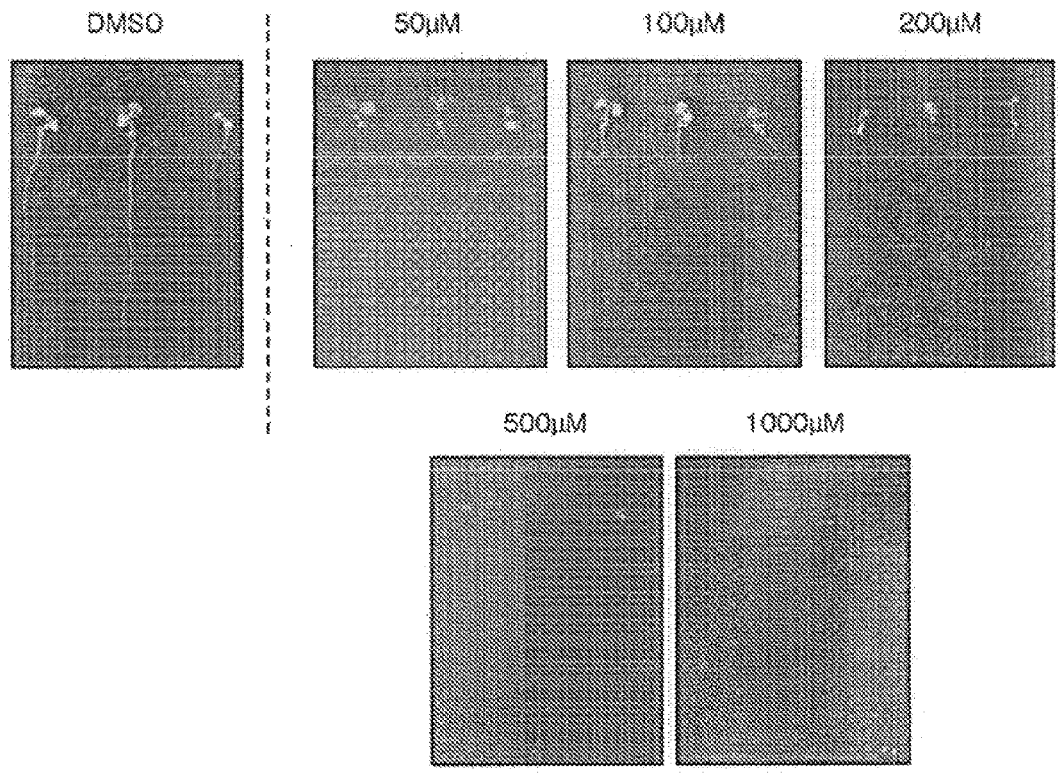
[Fig. 8]
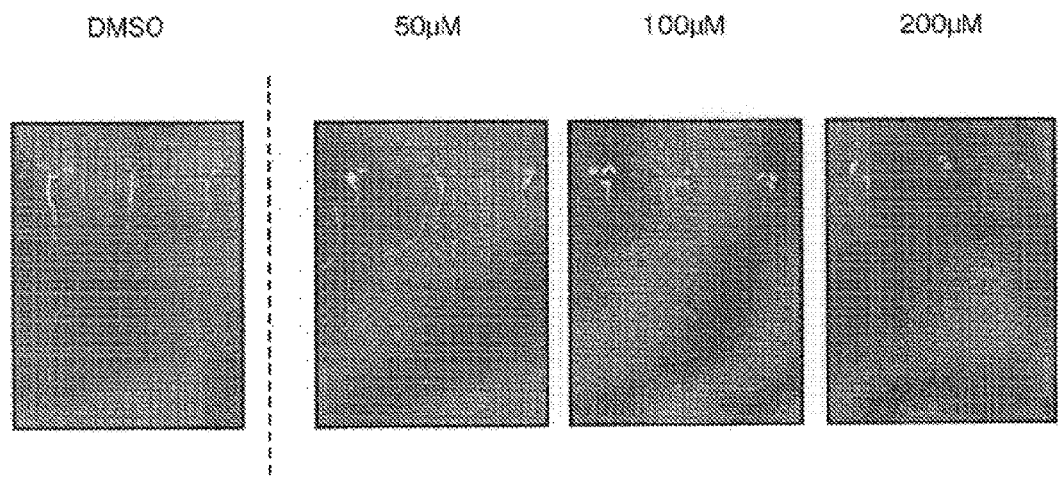

[Fig. 9]
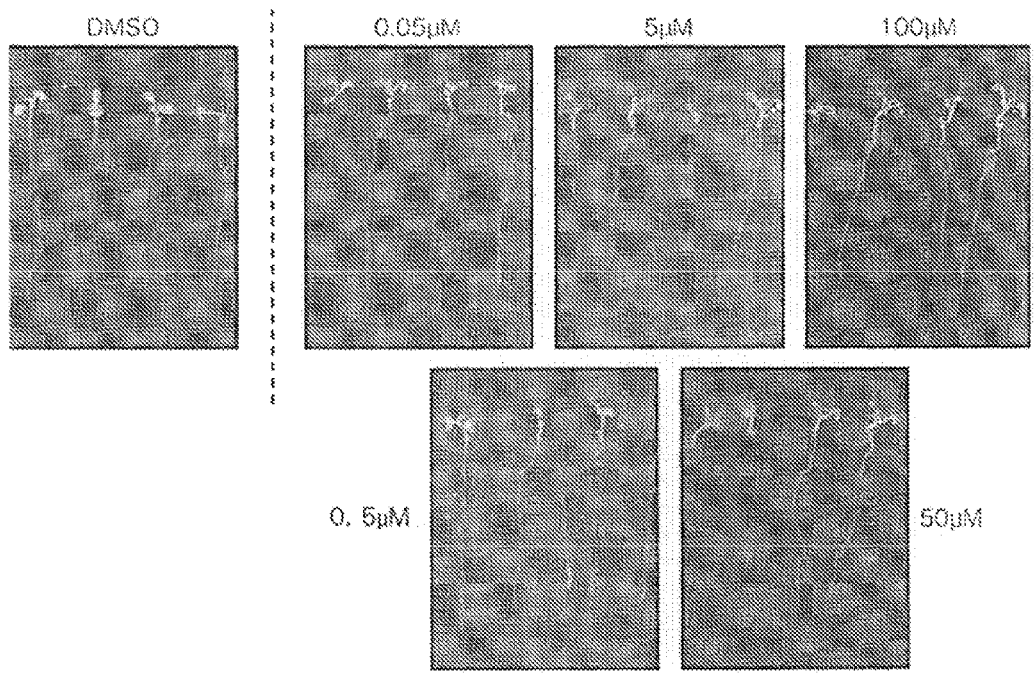
[Fig. 10]
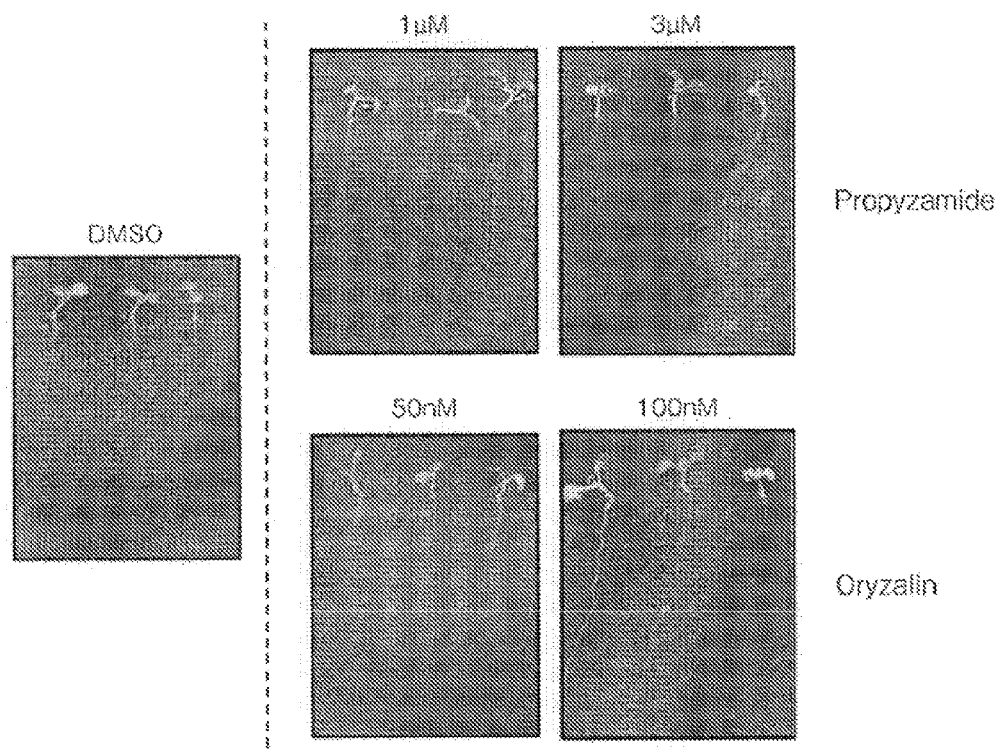

[Fig. 11]
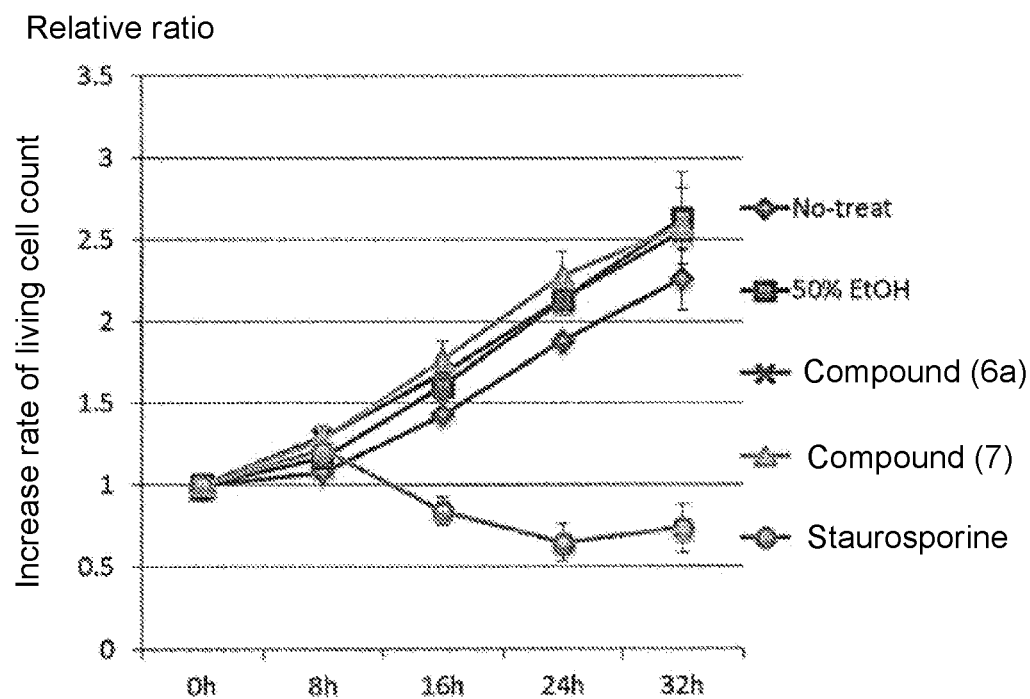
[Fig. 12]
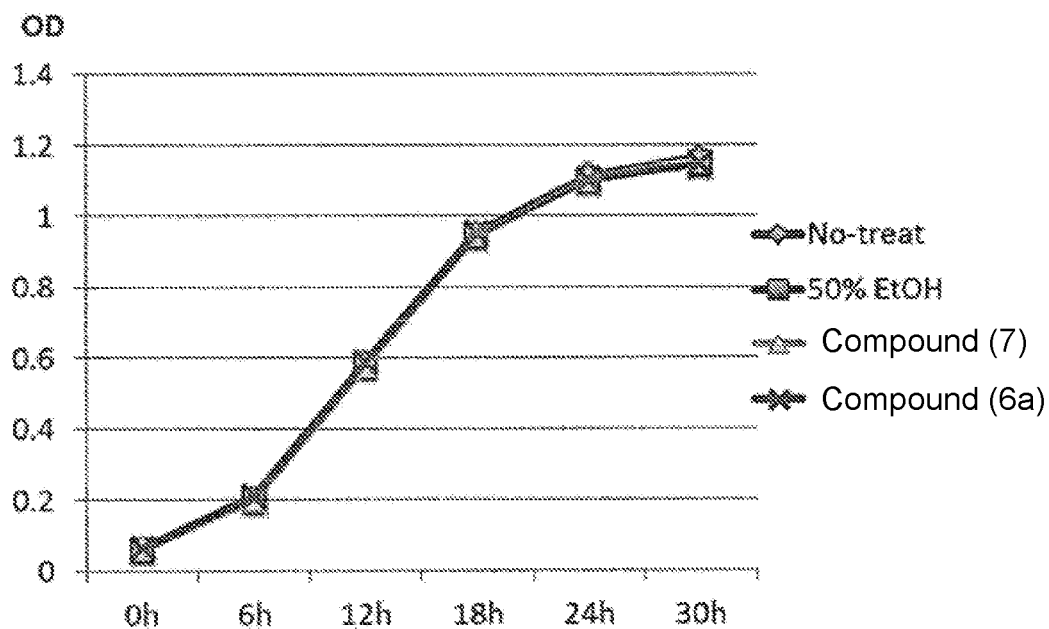

[Fig. 13]
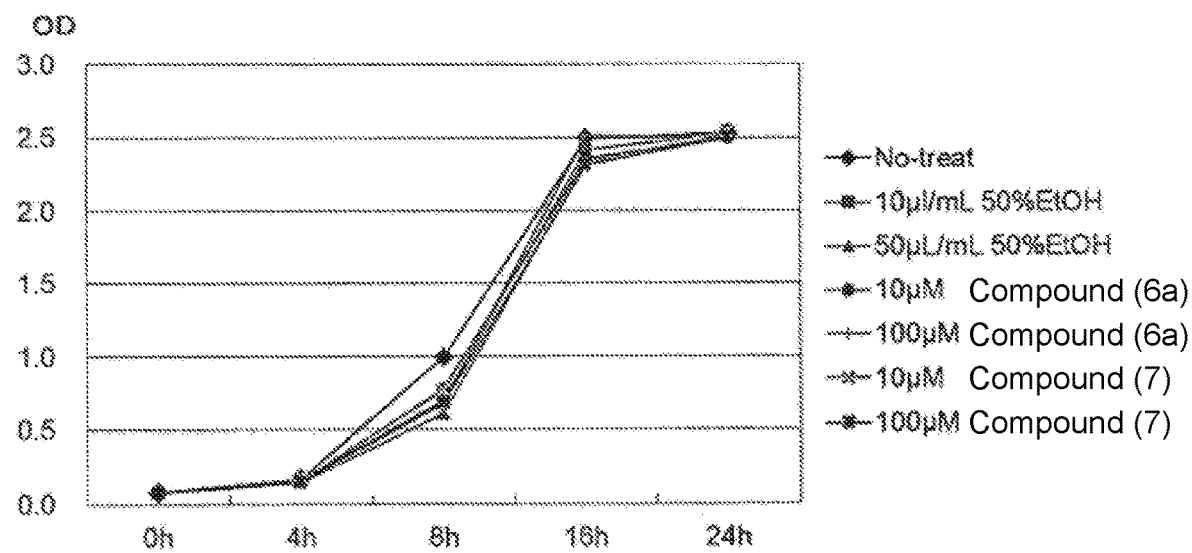
[Fig. 14]
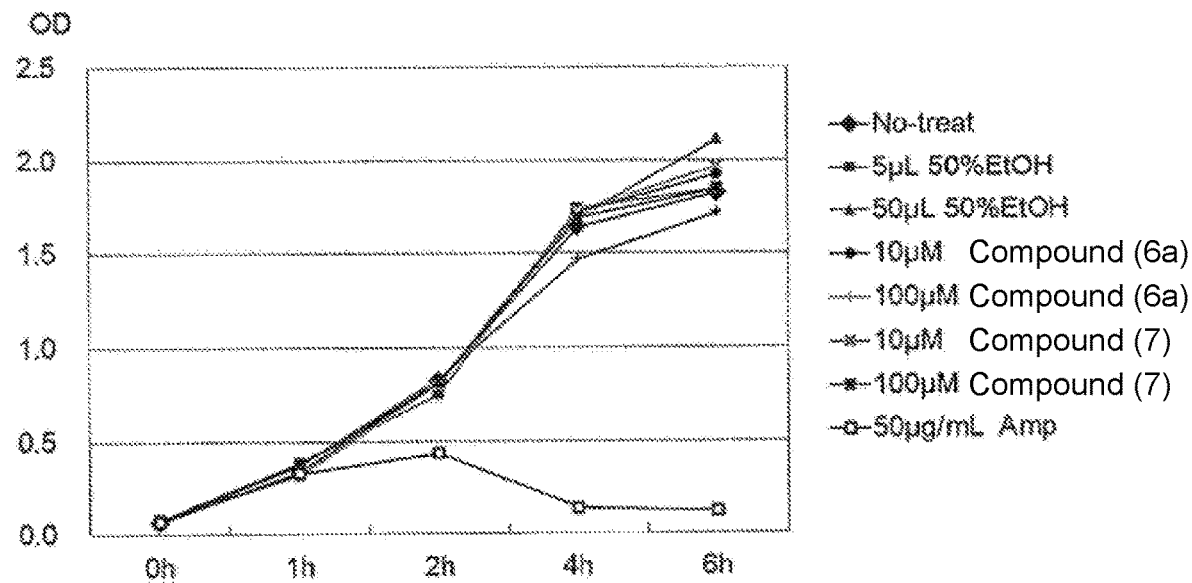

[Fig. 15]
[Fig. 16]
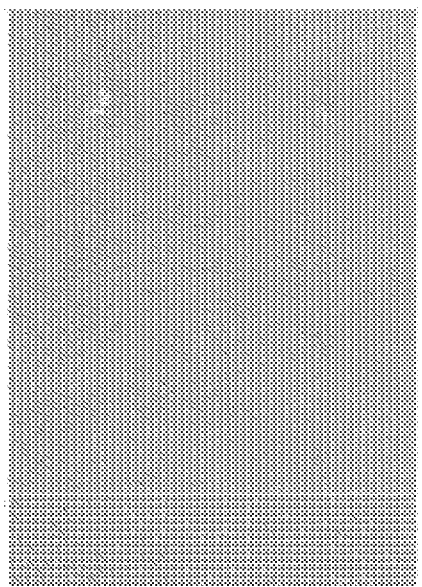

[Fig. 17]
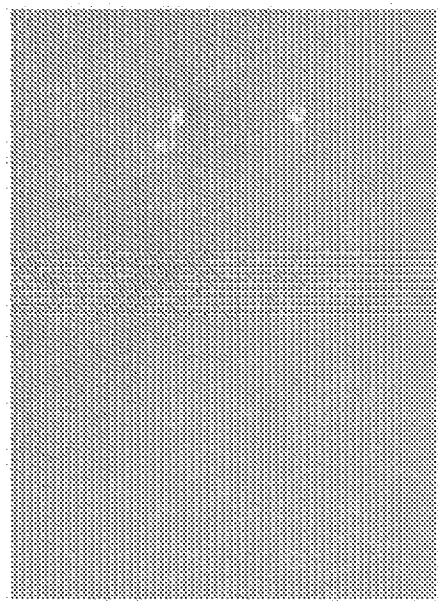
[Fig. 18]
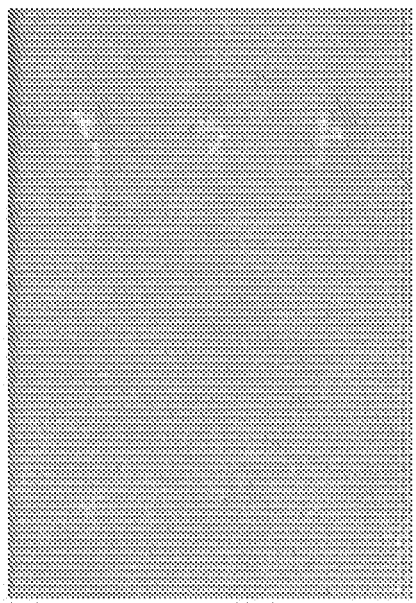

[Fig. 19]
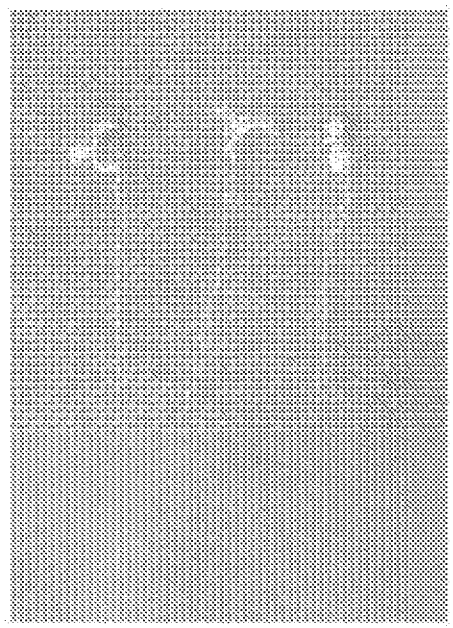
[Fig. 20]
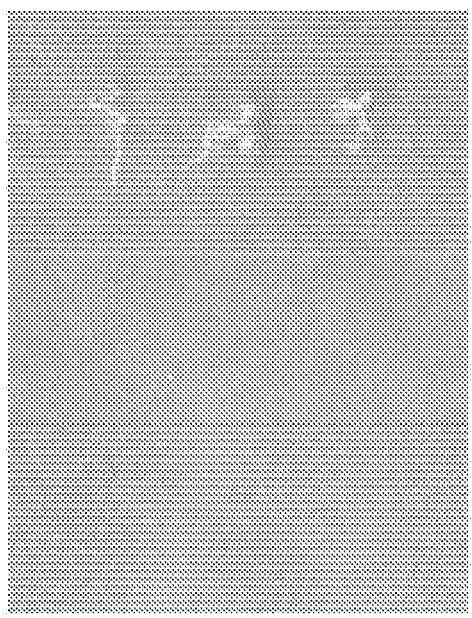

[Fig. 21]
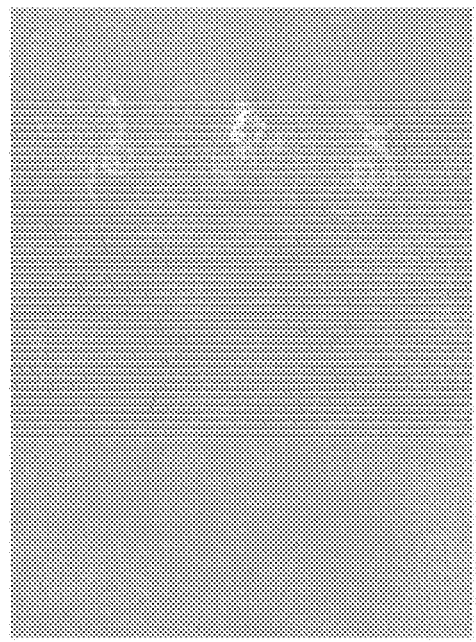
[Fig. 22]
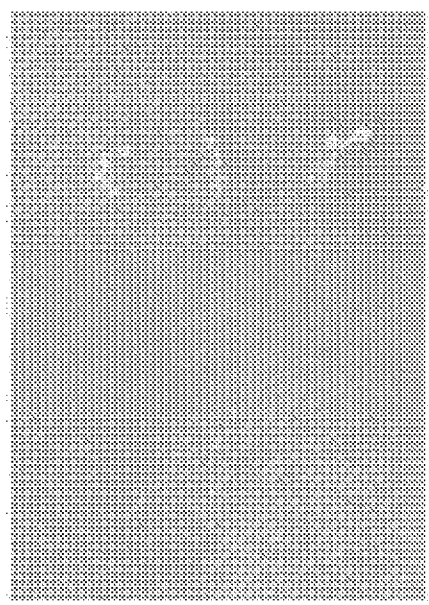

[Fig. 23]
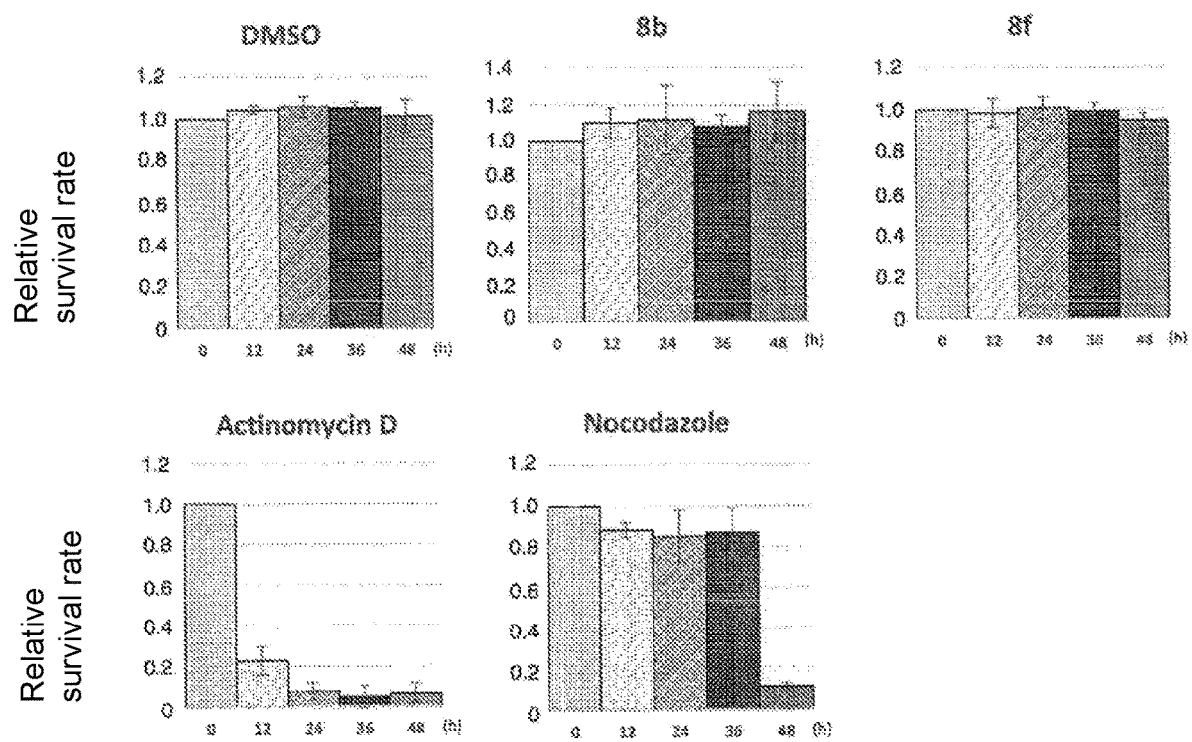

PLANT GROWTH INHIBITING AGENT, AND PLANT GROWTH INHIBITING METHOD USING SAME

CROSS-REFERENCE TO RELATED APPLICATIONS

This application is the U.S. National Stage of PCT/JP2018/004094, filed Feb. 6, 2018, which claims priority to JP 2017-020616, filed Feb. 7, 2017.

TECHNICAL FIELD

The present invention relates to a plant growth inhibiting agent, and a plant growth inhibiting method using the same. The present application claims priority to Japanese Patent Application No. 2017-020616, filed on Feb. 7, 2017, the contents of which are hereby incorporated.

BACKGROUND ART

Untended weeds are likely to spoil the landscape, cause vermination, or raise a safety issue by obstructing the field of view. For this reason, a wide range of studies on compounds which kill weeds or inhibit the growth thereof have been conducted and various compounds are proposed (for example, Patent Document 1 and Patent Document 2).

PRIOR ART DOCUMENTS

Patent Documents

Patent Document 1: Japanese unexamined Patent Application Publication No. 2014-094909
Patent Document 2: Japanese unexamined Patent Application Publication No. 2013-253052

SUMMARY OF THE INVENTION

Object to be Solved by the Invention

However, conventional compounds often affect not only plants but also animal cells by the same mode of action, and thus it was often difficult to apply as pesticides although they were sometimes used for academic researches. For this reason, the development of novel compounds applicable as pesticides has still been in demand.

Under such circumstances, an object of the present invention is to provide a novel plant growth inhibiting agent having a growth inhibiting activity on plants and a plant growth inhibiting method using the same.

Means to Solve the Objects

The present inventors conducted extensive studies to solve the above object, whereby consequently the present invention was accomplished.

More specifically, the present invention relates to the following inventions.

<1> A plant growth inhibiting agent comprising, as an active ingredient, at least one compound selected from the group consisting of a compound represented by the following formula (I') and a salt thereof:

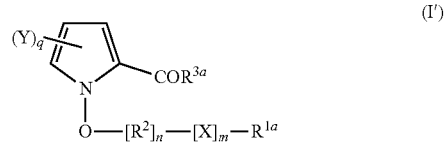

(wherein
$R^{1a}$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group;
$R^2$ represents a substituted or unsubstituted $C_1$ to $C_{20}$ alkylene group, a substituted or unsubstituted $C_6$ to $C_{14}$ arylene group, a substituted or unsubstituted $C_3$ to $C_{13}$ heteroarylene group, or a divalent linking group consisting of a combination thereof;
$R^{3a}$ represents OH, a substituted or unsubstituted $C_1$ to $C_6$ alkoxy group, or a group represented by a formula: $N(R^4)_2$ (wherein $R^4$ represents a hydrogen atom, or a substituted or unsubstituted $C_1$ to $C_6$ alkyl group, and two $R^4$ together can form a divalent organic group);
X represents an oxygen atom;
Y represents a substituent;
q represents any integer of 0 to 3;
n represents 0 or 1; and
m represents 0 or 1.)
<2> The plant growth inhibiting agent according to "1", wherein the compound represented by the formula (I') is a compound represented by the following formula (I):

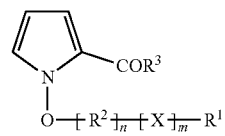

(wherein
$R^1$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group;
$R^2$ represents a substituted or unsubstituted $C_1$ to $C_{20}$ alkylene group, a substituted or unsubstituted $C_6$ to $C_{14}$ arylene group, a substituted or unsubstituted $C_3$ to $C_{13}$ heteroarylene group, or a divalent linking group consisting of a combination thereof;
$R^3$ represents OH or $NH_2$;
X represents an oxygen atom;
n represents 0 or 1; and
m represents 0 or 1.)
<3> The plant growth inhibiting agent according to "2", wherein in the formula (I), $R^3$ represents OH.
<4> The plant growth inhibiting agent according to "2" or "3", wherein in the formula (I), $R^1$ represents a substituted or unsubstituted $C_1$ to $C_{20}$ alkyl group, a substituted or unsubstituted $C_6$ to $C_{14}$ aryl group, or a substituted or unsubstituted $C_7$ to $C_{30}$ arylalkyl group.

<5> The plant growth inhibiting agent according to any one of "2" to "4", wherein in the formula (I), $R^1$ represents a substituted or unsubstituted $C_1$ to $C_{20}$ alkyl group, or a substituted or unsubstituted $C_7$ to $C_{30}$ arylalkyl group, and $R^3$ represents OH.

<6> The plant growth inhibiting agent according to any one of "2" to "5", wherein in the formula (I), n represents 0, and m represents 0.

<7> The plant growth inhibiting agent according to "6", wherein in the formula (I), $R^1$ represents a $C_1$ to $C_4$ alkyl group, or a benzyl group.

<8> A compound represented by the following formula (III), or a salt thereof:

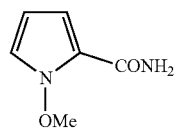

(III)

<9> A compound represented by the following formula (IV), or a salt thereof:

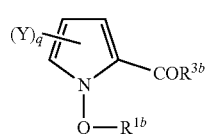

(IV)

(wherein $R^{1b}$ represents a substituted or unsubstituted $C_2$ to $C_{20}$ alkyl group, a substituted or unsubstituted $C_6$ to $C_{14}$ aryl group, a substituted or unsubstituted 5- to 10-membered heteroaryl group, a substituted or unsubstituted $C_6$ to $C_{10}$ aryl $C_1$ to $C_6$ alkyl group, or a substituted or unsubstituted 5- to 10-membered heteroaryl $C_1$ to $C_6$ alkyl group;

$R^{3b}$ represents OH, a substituted or unsubstituted $C_1$ to $C_6$ alkoxy group, or a group represented by a formula: $N(R^4)_2$ (wherein $R^4$ represents a hydrogen atom, or a substituted or unsubstituted $C_1$ to $C_6$ alkyl group, and two $R^4$ together can form a divalent organic group);

Y represents a substituent; and q represents any integer of 0 to 3.)

Effect of the Invention

According to the present invention, a plant growth inhibiting agent having a growth inhibiting activity on plants and a plant growth inhibiting method using the same are provided.

BRIEF DESCRIPTION OF DRAWINGS

FIG. 1 shows photographs showing affect of the compound (6a) of Example 1 on the growth of thale cress.

FIG. 2 shows stereomicroscopic photographs of roots of thale cress grown by adding the compound (6a) of Example 1.

FIG. 3 shows photographs showing affect of the compound (7) of Example 2 on the growth of thale cress.

FIG. 4 shows photographs showing affect of the compound (6b) of Example 3 on the growth of thale cress.

FIG. 5 shows photographs showing affect of the compound (6d) of Example 4 on the growth of thale cress.

FIG. 6 shows photographs showing affect of the compound (6e) of Example 5 on the growth of thale cress.

FIG. 7 shows photographs showing affect of the compound (6f) of Example 6 on the growth of thale cress.

FIG. 8 shows photographs showing affect of the compound (6g) of Example 7 on the growth of thale cress.

FIG. 9 shows photographs showing affect of the compound (6c) of Comparative Example 1 on the growth of thale cress.

FIG. 10 shows photographs showing affect of propyzamide and oryzalin on the growth of thale cress.

FIG. 11 shows evaluation results in cell proliferation inhibiting activity of the compound (6a) of Example 1, the compound (7) of Example 2, ethanol, and staurosporine on human cultured cancer cells (HeLa cell).

FIG. 12 shows evaluation results in growth inhibiting activity of the compound (6a) of Example 1, the compound (7) of Example 2, and ethanol on *Schizosaccharomyces pombe*.

FIG. 13 shows evaluation results in growth inhibiting activity of the compound (6a) of Example 1, the compound (7) of Example 2, and ethanol on *Saccharomyces cerevisiae*.

FIG. 14 shows evaluation results in growth inhibiting activity of the compound (6a) of Example 1, the compound (7) of Example 2, ethanol, and Amp on *E. coli*.

FIG. 15 shows a photograph showing affect of a compound (8a) on the growth of thale cress.

FIG. 16 shows a photograph showing affect of a compound (8b) on the growth of thale cress.

FIG. 17 shows a photograph showing affect of a compound (8c) on the growth of thale cress.

FIG. 18 shows a photograph showing affect of a compound (8d) on the growth of thale cress.

FIG. 19 shows a photograph showing affect of a compound (8e) on the growth of thale cress.

FIG. 20 shows a photograph showing affect of a compound (8f) on the growth of thale cress.

FIG. 21 shows a photograph showing affect of a compound (8g) on the growth of thale cress.

FIG. 22 shows a photograph showing affect of a compound (8h) on the growth of thale cress.

FIG. 23 shows evaluation results in cytotoxicity of the compound (8b), the compound (8f), actinomycin D, and Nocodazole on human cultured cancer cells (HeLa cell).

MODE OF CARRYING OUT THE INVENTION

Hereinafter, the present invention will be described in detail with reference to examples and the like but is not limited to the following examples and the like, and can be carried out with any alterations without departing from the scope of the invention. Note that, in the present Description, "$C_p$ to $C_q$" (p and q are each an integer and satisfy p<q) represents that the number of carbon atoms of an organic group is p to q. For example, the $C_1$ to $C_{20}$ in "a substituted or unsubstituted $C_1$ to $C_{20}$ alkyl group" represents that the number of carbons in the alkyl group part is 1 to 20 without including the carbons in a substituted part.

1. Plant Growth Inhibiting Agent

A plant growth inhibiting agent of the present invention (hereinafter, sometimes described as "a plant growth inhibiting agent of the present invention") comprises, as an active ingredient, at least one compound selected from the group consisting of a compound represented by the following formula (I') and a salt thereof. The plant growth inhibiting agent of the present invention may be composed of one of the compounds represented by the following formula (I'), a mixture of two or more compounds represented by the following formula (I'), or a mixture of the compound represented by the following formula (I') and salts thereof.

Further, when hydrates, various crystalline forms, and various structural isomers exist, they are also included in the compounds or salts thereof of the present invention.

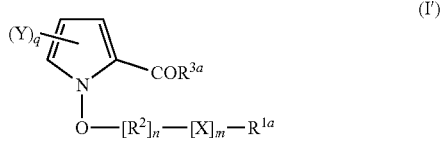
(I')

(wherein
$R^{1a}$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group;
$R^2$ represents a substituted or unsubstituted $C_1$ to $C_{20}$ alkylene group, a substituted or unsubstituted $C_6$ to $C_{14}$ arylene group, a substituted or unsubstituted $C_3$ to $C_{13}$ heteroarylene group, or a divalent linking group consisting of a combination thereof;
$R^{3a}$ represents OH, a substituted or unsubstituted $C_1$ to $C_6$ alkoxy group, or a group represented by a formula: $N(R^4)_2$ (wherein $R^4$ represents a hydrogen atom or a substituted or unsubstituted $C_1$ to $C_6$ alkyl group, and two $R^4$ together can form a divalent organic group); X represents an oxygen atom; Y represents a substituent; q represents an any integer of 0 to 3; n represents 0 or 1; and m represents 0 or 1.

The compounds represented by the above formula (I') include a compound represented by the following formula (I).

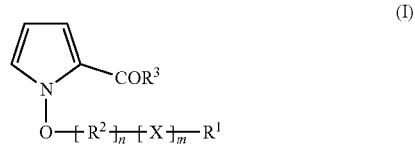
(I)

wherein $R^1$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group; $R^2$ represents a substituted or unsubstituted $C_1$ to $C_{20}$ alkylene group, a substituted or unsubstituted $C_6$ to $C_{14}$ arylene group, a substituted or unsubstituted $C_3$ to $C_{13}$ heteroarylene group, or a divalent linking group consisting of a combination thereof; $R^3$ represents OH or $NH_2$; X represents an oxygen atom; n represents 0 or 1; and m represents 0 or 1.

The feature of a plant growth inhibiting agent of the present invention is to comprise a compound represented by the above formula (I') as an active ingredient. The feature of the compound represented by the above formula (I') is to have a structure wherein an oxygen atom binds to the N position of a pyrrole ring, and can inhibit the growth of plants because such a compound is comprised as an active ingredient.

Detailed mode of action of a compound represented by the above formula (I') on the growth inhibiting of plants is not known, but the way the plant growth is suppressed is similar to the phenotype of dysfunction of microtubule function whereby the compound represented by the above formula (I') is presumed to have microtubule organization inhibiting effect due to which a plant growth inhibiting agent of the present invention can inhibit the growth of plants.

Further, the compound represented by the above formula (I') does not have toxicity to human and animals while having a growth inhibiting activity on plants, which is also one of the features.

[Compounds Represented by Formula (I') and Compounds Represented by Formula (I)]

Hereinafter, a compound represented by a formula (I') and a compound represented by a formula (I), which are active ingredients of a plant growth inhibiting agent of the present invention will be described. Note that the compounds represented by the formula (I') (including the compounds represented by the formula (I)) are sometimes described as "compound (A)".

Each group of the formula (I') and the formula (I) will be respectively described in detail.

($R^{1a}$ and $R^1$)

In the formula (I') and the formula (I), $R^{1a}$ and $R^1$ each represent a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group.

Of these, $R^{1a}$ and $R^1$ each preferably represent a substituted or unsubstituted $C_1$ to $C_{20}$ alkyl group, a substituted or unsubstituted $C_6$ to $C_{14}$ aryl group, or a substituted or unsubstituted $C_7$ to $C_{30}$ arylalkyl group, and more preferably a substituted or unsubstituted $C_1$ to $C_{20}$ alkyl group, or a substituted or unsubstituted $C_7$ to $C_{30}$ arylalkyl group.

The "$C_1$ to $C_{20}$ alkyl group" in "a substituted or unsubstituted $C_1$ to $C_{20}$ alkyl group" means a linear, branched, or cyclic alkyl group having 1 to 20 carbon atoms and includes a methyl group, an ethyl group, a propyl group, an isopropyl group, a butyl group, a cyclopropyl group, and a cyclopropylmethyl group.

The $C_1$ to $C_{20}$ alkyl group has preferably 2 or more carbon atoms, and more preferably 3 or more carbon atoms. Further, such a group has preferably 12 or less carbon atoms, and more preferably 6 or less carbon atoms.

Furthermore, the $C_1$ to $C_{20}$ alkyl group is preferably linear.

Examples of the substituent substitutable for a $C_1$ to $C_{20}$ alkyl group include a halogen atom, an OH group, a $C_1$ to $C_6$ alkoxy group, a substituted or unsubstituted $C_6$ to $C_{14}$ aryl group, a substituted or unsubstituted 5- or 6-membered heteroaryl group, a substituted or unsubstituted $C_6$ to $C_{10}$ aryloxy group, an amino group, and a cyano group, but not limited thereto. Further, the substituent may have one or more same or different substituents.

Each of the above substituents is specifically exemplified.

Examples of the halogen atom include a fluoro group, a chloro group, a bromo group, and an iodo group.

Examples of the $C_1$ to $C_6$ alkoxy group include a methoxy group, an ethoxy group, a n-propoxy group, an i-propoxy group, and a n-butoxy group, a s-butoxy group, an i-butoxy group, and a t-butoxy group.

Examples of the $C_6$ to $C_{10}$ aryl group include a phenyl group, and a naphthyl group.

Examples of the 5- or 6-membered heteroaryl group include a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; and 6-membered heteroaryl groups such as a pyridyl group, a pyrazinyl group, a pyrimidinyl group, a pyridazinyl group, and a triazinyl group.

Examples of the $C_6$ to $C_{10}$ aryloxy group include a phenoxy group, and a naphthoxy group.

Examples of the substituent substitutable for a $C_6$ to $C_{10}$ aryl group, a 5- to 6-membered heteroaryl group, or a $C_6$ to $C_{10}$ aryloxy group include a $C_1$ to $C_6$ alkyl group such as a methyl group, an ethyl group, a n-propyl group, an i-propyl group, a n-butyl group, a s-butyl group, an i-butyl group, a t-butyl group, a n-pentyl group, and a n-hexyl group; a hydroxyl group; a $C_1$ to $C_6$ alkoxy group such as a methoxy group, an ethoxy group, a n-propoxy group, an i-propoxy group, a n-butoxy group, a s-butoxy group, an i-butoxy group, and a t-butoxy group; a halogeno group such a fluoro group, a chloro group, a bromo group, and an iodo group; a $C_1$ to $C_6$ haloalkyl group such as a chloromethyl group, a chloroethyl group, a trifluoromethyl group, an 1,2-dichloro-n-propyl group, a 1-fluoro-n-butyl group, and a perfluoro-n-pentyl group; a $C_1$ to $C_6$ haloalkoxy group such as a trifluoromethoxy group, a 2-chloro-n-propoxy group, and a 2,3-dichlorobutoxy group; a cyano group; and a nitro group.

The "$C_6$ to $C_{14}$ aryl group" in "a substituted or unsubstituted $C_6$ to $C_{14}$ aryl group" means an aromatic hydrocarbon ring wherein the number of carbon atoms constituting the ring is 6 to 14, and may be monocyclic or polycyclic.

Examples of the $C_6$ to $C_{14}$ aryl group include a phenyl group, a naphthyl group, an anthracenyl group, and a phenanthrenyl group, and one of preferable $C_6$ to $C_{14}$ aryl groups includes a phenyl group.

Examples of the substituent substitutable for a $C_6$ to $C_{14}$ aryl group include a halogen atom, a hydroxyl group, a $C_1$ to $C_6$ alkyl group, a $C_1$ to $C_6$ haloalkyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, an amino group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those listed respectively in "the substituent substitutable with a $C_1$ to $C_{20}$ alkyl group".

Examples of the $C_1$ to $C_6$ alkyl group include a methyl group, an ethyl group, a n-propyl group, an i-propyl group, a n-butyl group, a s-butyl group, an i-butyl group, a t-butyl group, a n-pentyl group, and a n-hexyl group.

Examples of the $C_1$ to $C_6$ haloalkyl group include a chloromethyl group, a chloroethyl group, a trifluoromethyl group, an 1,2-dichloro-n-propyl group, a 1-fluoro-n-butyl group, and a perfluoro-n-pentyl group.

Example of the $C_1$ to $C_6$ haloalkoxy group include a trifluoromethoxy group, a 2-chloro-n-propoxy group, and a 2,3-dichlorobutoxy group.

The "$C_3$ to $C_{13}$ heteroaryl group" in "a substituted or unsubstituted $C_3$ to $C_{13}$ heteroaryl group" means an aromatic ring which includes, as a ring constituent element, one or more hetero atoms selected from the group consisting of an oxygen atom, a sulfur atom, and a nitrogen atom and has the number of carbon atoms constituting the ring is 3 to 13, and may be monocyclic or polycyclic.

Examples of the $C_3$ to $C_{13}$ heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, a pyridyl group, a pyrazinyl group, a pyrimidinyl group, a pyridazinyl group, a triazinyl group, a carbazolyl group, an indolyl group, and a quinolyl group.

Examples of the substituent substitutable for a $C_3$ to $C_{13}$ heteroaryl group include a halogen atom, an OH group, a $C_1$ to $C_6$ alkyl group, a $C_1$ to $C_6$ haloalkyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, an amino group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and the $C_6$ to $C_{10}$ aryloxy group include the same substituents as those listed respectively in "the substituent substitutable with a $C_1$ to $C_{20}$ alkyl group."

Specific examples of the above $C_1$ to $C_6$ alkyl group, $C_1$ to $C_6$ haloalkyl group, and $C_1$ to $C_6$ haloalkoxy group include the same substituents as those exemplified respectively in "the substituent substitutable for a $C_6$ to $C_{14}$ aryl group."

The "$C_7$ to $C_{30}$ arylalkyl group" in "a substituted or unsubstituted $C_7$ to $C_{30}$ arylalkyl group" is an alkyl group substituted with one or more aryl groups and means a substituent wherein the number of carbon atoms is 7 to 30. A preferable $C_7$ to $C_{30}$ arylalkyl group is a $C_7$ to $C_{30}$ arylalkyl group wherein one or more hydrogen atoms of the above $C_1$ to $C_{20}$ alkyl group is substituted with a phenyl group or a naphthyl group.

Examples of the $C_7$ to $C_{30}$ arylalkyl group include a benzyl group, a phenylethyl group, a naphthylmethyl group, and a naphthylethyl group. One of preferable $C_7$ to $C_{30}$ arylalkyl groups is a benzyl group.

Examples of the substituent substitutable for a $C_7$ to $C_{30}$ arylalkyl group include a halogen atom, an OH group, a $C_1$ to $C_6$ alkyl group, a $C_1$ to $C_6$ haloalkyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, an amino group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those exemplified respectively in "the substituent substitutable for a $C_1$ to $C_{20}$ alkyl group."

Specific examples of the above $C_1$ to $C_6$ alkyl group, $C_1$ to $C_6$ haloalkyl group, and $C_1$ to $C_6$ haloalkoxy group include the same substituents as those exemplified respectively in "the substituent substitutable for a $C_6$ to $C_{14}$ aryl group."

The "$C_4$ to $C_{30}$ heteroarylalkyl group" in "a substituted or unsubstituted $C_4$ to $C_{30}$ heteroarylalkyl group" is an alkyl group substituted with one or more heteroaryl groups and means a substituent wherein the number of carbon atoms is 4 to 30. A preferable $C_4$ to $C_{30}$ heteroarylalkyl group is a $C_4$ to $C_{30}$ heteroarylalkyl group wherein one or more hydrogen atoms of the above $C_1$ to $C_{20}$ alkyl group is substituted with a heteroaryl group.

Examples of the $C_4$ to $C_{30}$ heteroarylalkyl group include a furylmethyl group, a pyridylmethyl group, and a pyridylethyl group.

Examples of the substituent substitutable for a $C_4$ to $C_{30}$ heteroarylalkyl group include a halogen atom, an OH group, a $C_1$ to $C_6$ alkyl group, a $C_1$ to $C_6$ haloalkyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, an amino group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those exemplified respectively in "the substituent substitutable for a $C_1$ to $C_{20}$ alkyl group."

Specific examples of the above $C_1$ to $C_6$ alkyl group, $C_1$ to $C_6$ haloalkyl group, and $C_1$ to $C_6$ haloalkoxy group include the same substituents as those exemplified respectively in "the substituent substitutable for a $C_6$ to $C_{14}$ aryl group."

($R^2$)

In the formula (I') and the formula (I), $R^2$ represents a substituted or unsubstituted $C_1$ to $C_{20}$ alkylene group, a substituted or unsubstituted $C_6$ to $C_{14}$ arylene group, a substituted or unsubstituted $C_3$ to $C_{13}$ heteroarylene group, or a divalent linking group consisting of a combination thereof.

The "$C_1$ to $C_{20}$ alkylene group" in "a substituted or unsubstituted $C_1$ to $C_{20}$ alkylene group" is a divalent linking group formed by removing any one hydrogen atom from the above "$C_1$ to $C_{20}$ alkyl group" and include a methylene group, an ethylene group, a propylene group, an isopropylene group, a butylene group, and an isobutylene group.

Examples of the substituent substitutable for a $C_1$ to $C_{20}$ alkylene group include the same substituents as the above $C_1$ to $C_{20}$ alkyl group.

The $C_1$ to $C_{20}$ alkylene group has preferably 2 or more carbon atoms, and more preferably 3 or more carbon atoms. Further, such a group has preferably 12 or less carbon atoms, more preferably 6 or less carbon atoms, and further preferably 4 or less carbon atoms.

Further, the $C_1$ to $C_{20}$ alkylene group is preferably linear.

The "$C_6$ to $C_{14}$ arylene group" in "a substituted or unsubstituted $C_6$ to $C_{14}$ arylene group" is a divalent linking group formed by removing any one hydrogen atom from the above "$C_6$ to $C_{14}$ aryl group."

Examples of the $C_6$ to $C_{14}$ arylene group include a phenylene group, a naphthylene group, an anthracenylene group, and a phenanthrenylene group, and one of preferable $C_6$ to $C_{14}$ arylene groups includes a phenylene group.

Examples of the substituent substitutable for a $C_6$ to $C_{14}$ arylene group include the same substituents as the above $C_6$ to $C_{14}$ aryl group.

The "$C_3$ to $C_{13}$ heteroarylene group" in "a substituted or unsubstituted $C_3$ to $C_{13}$ heteroarylene group" is a divalent linking group formed by removing any one hydrogen atom from the above "$C_3$ to $C_{13}$ heteroaryl group".

Examples of the substituent substitutable for a $C_3$ to $C_{13}$ heteroarylene group include the same substituents as the above $C_3$ to $C_{13}$ heteroaryl group.

Further, $R^2$ may represent a divalent linking group obtained by combining a $C_1$ to $C_{20}$ alkylene group, a $C_6$ to $C_{14}$ arylene group, or a $C_3$ to $C_{13}$ heteroarylene group, and examples of such a divalent linking group include a divalent linking group wherein a $C_1$ to $C_{20}$ alkylene group and a $C_6$ to $C_{14}$ arylene group bond.

A preferable $R^2$ represents a divalent linking group consisting of $C_1$ to $C_{20}$ alkylene groups, or a $C_1$ to $C_{20}$ alkylene group and a $C_6$ to $C_{14}$ arylene group.

When $R^2$ is a divalent linking group consisting of a $C_1$ to $C_{20}$ alkylene group and a $C_6$ to $C_{14}$ arylene group, the bonding moiety to the oxygen atom bound to the N of the pyrrole ring may be the alkylene moiety or arylene moiety. Examples of such a divalent linking group include a divalent linking group wherein a methylene group and a phenylene group bond.

($R^{3a}$ and $R^3$)

In the formula (I'), $R^{3a}$ represents OH, a substituted or unsubstituted $C_1$ to $C_6$ alkoxy group, or a group represented by a formula: $N(R^4)_2$ (wherein $R^4$ represents a hydrogen atom or a substituted or unsubstituted $C_1$ to $C_6$ alkyl group, and two $R^4$ together can form a divalent organic group).

The above "$C_1$ to $C_6$ alkoxy group" in "a substituted or unsubstituted $C_1$ to $C_6$ alkoxy group" means a linear, branched, or cyclic alkoxy group having 1 to 6 carbon atoms and includes a methoxy group, an ethoxy group, a propoxy group, an isopropoxy group, a butoxy group, and a cyclopropoxy group.

Examples of the substituent substitutable for a $C_1$ to $C_6$ alkoxy group include a halogen atom, a $C_1$ to $C_6$ alkoxy group, a substituted or unsubstituted $C_6$ to $C_{10}$ aryl group, a substituted or unsubstituted 5- to 6-membered heteroaryl group, and a cyano group, but not limited thereto. Further, the substituent optionally has one or more same or different substituents.

Specific examples of the above halogen atom, $C_1$ to $C_6$ alkoxy group, substituted or unsubstituted $C_6$ to $C_{10}$ aryl group, and substituted or unsubstituted 5- to 6 membered heteroaryl group include the same substituents as those respectively exemplified in "the substituent substitutable for a $C_1$ to $C_{20}$ alkyl group."

The $R^4$ in "a group represented by a formula: $N(R^4)_2$" represents a hydrogen atom or a substituted or unsubstituted $C_1$ to $C_6$ alkyl group.

The "$C_1$ to $C_6$ alkyl group" means a linear, branched, or cyclic alkyl group having 1 to 6 carbon atoms and includes a methyl group, and an ethyl group.

Examples of the substituent substitutable for a $C_1$ to $C_6$ alkyl group include a halogen atom, a $C_1$ to $C_6$ alkoxy group, a substituted or unsubstituted $C_6$ to $C_{10}$ aryl group, a substituted or unsubstituted 5- to 6-membered heteroaryl group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, and substituted or unsubstituted 5- to 6-membered heteroaryl group include the same substituents as those respectively exemplified in "the substituent substitutable for a $C_1$ to $C_{20}$ alkyl group."

Examples of the "divalent organic group formed by two $R^4$ bonding" include $C_2$ to $C_5$ alkylene groups such as a dimethylene group, a trimethylene group, a tetramethylene group, and a pentamethylene group, and $C_2$ to $C_3$ alkyleneoxy $C_2$ to $C_3$ alkylene groups such as a dimethyleneoxydimethylene group.

In the formula (I), $R^3$ represents OH or $NH_2$, and $R^3$ preferably represents OH. Particularly, in the formula (I), $R^1$ represents a $C_1$ to $C_{20}$ alkyl group or a $C_7$ to $C_{30}$ arylalkyl group, and $R^3$ preferably represents OH.

(Y, q)

In the formula (I), Y represents a substituent, and q represents any integer of 0 to 3.

Examples of the above substituent include a halogen atom, a $C_1$ to $C_6$ alkyl group, a $C_1$ to $C_6$ haloalkyl group, an OH group, a $C_1$ to $C_6$ alkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those respectively exemplified in "the substituent substitutable for a $C_1$ to $C_{20}$ alkyl group."

Specific examples of the above $C_1$ to $C_6$ alkyl group and $C_1$ to $C_6$ haloalkyl group include the same substituents as those respectively exemplified in "the substituent substitutable for a $C_1$ to $C_{14}$ aryl group.

(X)

In the formula (I') and the formula (I), X represents an oxygen atom.

(n, m)

In the formula (I') and the formula (I), n represents 0 or 1. In addition, when n is 0, it represents a single bond. Further, in the formula (I), m represents 0 or 1. In addition, when m is 0, it represents a single bond. For example, when n is 1 and m is 1, a structure in which the oxygen atom bound to the N position of the pyrrole ring and $R^1$ are bound through $R^2$ and X is represented, and when n is 0 and m is 0, a structure in which the oxygen atom bound to the N position of the pyrrole ring is directly bound to $R^1$ is represented.

Of the compounds represented by the formula (I') and the formula (I) (compound (A)), a preferable compound includes a compound wherein in the formula (I), n represents 0 and m represents 0. More specifically, a compound represented by the following formula (II) is included.

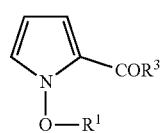
(II)

(wherein $R^1$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group; and $R^3$ represents OH, or $NH_2$.)

$R^1$ and $R^3$ in the formula (II) have the same meanings as $R^1$ and $R^3$ in the formula (I) and are as described above in the explanation of the formula (I), and thus the explanation herein is left out. Preferable $R^1$ and $R^3$ are also the same as in the formula (I).

Of the compounds represented by the formula (II), examples of the preferable compounds include a compound wherein in the formula (II), $R^1$ represents a $C_1$ to $C_4$ alkyl group or a benzyl group.

Specific examples of the compound represented by the formula (II) (compound (A)) include the following compounds.

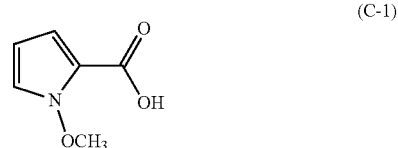
(C-1)

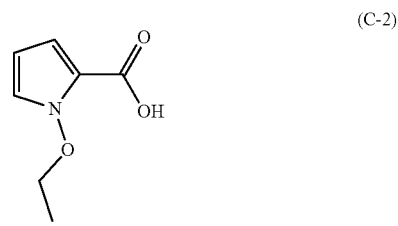
(C-2)

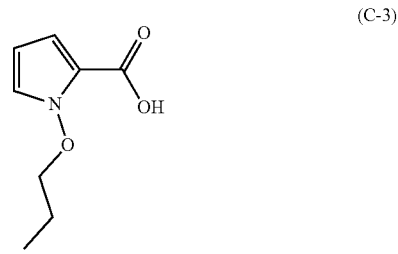
(C-3)

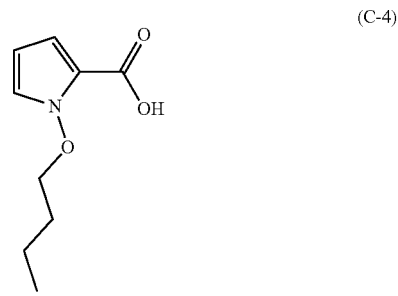
(C-4)

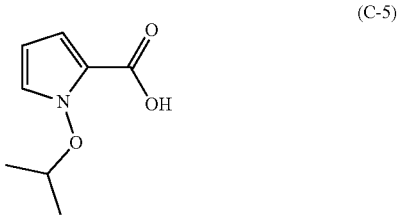
(C-5)

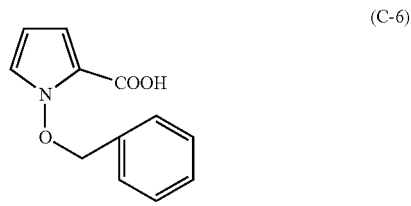
(C-6)

Further, examples of other compounds (A) include the following compounds.

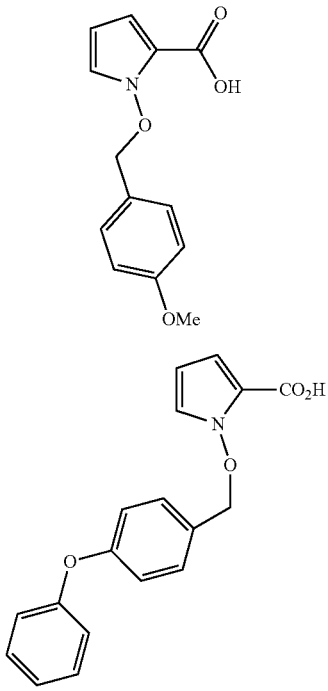

(C-7)

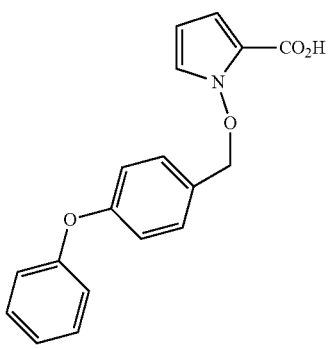

(C-8)

[Salts]

A salt of a compound represented by the formula (I') or the formula (I) is not particularly limited as long as it is an agriculturally and horticulturally acceptable salt. Examples include a salt of an inorganic acid such as a hydrochloric acid and a sulfuric acid; a salt of an organic acid such as an acetic acid and a lactic acid; a salt of an alkali metal such as lithium, sodium, and potassium; a salt of an alkaline earth metal such as calcium and magnesium; a salt of a transition metal such as iron and copper; ammonia; and a salt of an organic base such as triethylamine, tributylamine, pyridine, and hydrazine.

[Production Method of the Compound Represented by the Formula (I') or the Formula (I)]

A compound represented by the formula (I') or the formula (I) is optionally a commercial compound, or, for example, can be synthesized according to the method described in the section of novel compounds.

[Dosage Form, Other Ingredients]

A plant growth inhibiting agent of the present invention can be used in a suitable dosage form depending on a purpose thereof such as a powder, a granule, a wettable powder, an emulsion, a water-soluble agent, or a suspension. The compound (A) may be directly used as a plant growth inhibiting agent but is typically used as dissolved or dispersed in a liquid carrier, or the compound (A) is used as mixed in or adsorbed onto a solid carrier.

A liquid carrier is not particularly limited within a range in which it does not adversely affect the purpose of the present invention and examples include water, an alcohol (ethanol and ethylene glycol), a ketone (acetone, methyl ethyl ketone, and cyclohexanone), an ether (diethyleneglycol dimethyl ether), an ester (ethyl acetate and butyl acetate), an aromatic hydrocarbon (toluene and xylene), an aliphatic hydrocarbon (kerosene and a mineral oil), and a fatty oil (for example, a rapeseed oil, a soybean oil, an olive oil, a corn oil, a palm oil, a castor oil). These liquid carriers are may be used alone, or used by mixture of two or more thereof.

A solid carrier is not particularly limited within a range in which it does not adversely affect the purpose of the present invention and examples include a clay, a talc, a bentonite, a montmorillonite, a kaolinite, a diatomaceous earth, a white clay, a vermiculite, a plaster, calcium carbonate, an amorphous silica, ammonium sulfate, a soybean powder, a wood flour, a sawdust, a wheat, lactose, sucrose, glucose, and urea. These solid carriers may be used alone, or used by mixture of two or more thereof.

Further, a plant growth inhibiting agent of the present invention may contain other ingredients as required, within a range in which they do not adversely affect the effect of the compound (A), such as a surfactant, a dispersant, a wettable agent, and an excipient.

A content of the compound (A) comprised in a plant growth inhibiting agent of the present invention is not particularly limited within a range in which the effect of the compound (A) can be exhibited. For example, when a plant growth inhibiting agent of the present invention is liquid, it may comprise 50 µmol/L or more, 100 µmol/L or more, or 200 µmol/L or more, of the compound (A) as an active ingredient.

A plant growth inhibiting agent of the present invention may further be used by the combination of other herbicidal compounds depending on a purpose thereof, due to which a range of applicable weed types, a period of chemical agent treatment, and herbicidal activities may be improved in a more preferable direction. Such other herbicidally active ingredients (generic name, etc.) include those as follows.

When salts, alkylesters, hydrates, different crystalline forms, various structural isomers thereof, or the like exist, they are obviously included even when specific descriptions are not provided.

Other herbicidally active ingredients used in the present invention are not particularly limited, but examples include those exemplified in the following (a) to (o).

(a) Aryloxyphenoxypropionic acid ester-based such as clodinafop-propargyl, cyhalofop-butyl, diclofop-methyl, fenoxaprop-P-ethyl, fluazifop-P, fluazifop-P-butyl, haloxyfop-methyl, pyriphenop-sodium, propaquizafop, quizalofop-P-ethyl, and metamifop; cyclohexanedione-based such as alloxydim, butroxydim, clethodim, cycloxydim, profoxydim, sethoxydim, tepraloxydim, and tralkoxydim; phenylpyrazoline-based such as pinoxaden; and other ingredients considered to exhibit herbicidal effects by inhibiting the acetyl-CoA carboxylase of plants.

(b) Sulfonylurea-based such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron, foramsulfuron, halosulfuron-methyl, imazosulfuron, iodosulfuron-methyl, mesosulfuron, mesosulfuron-methyl, metsulfuron-methyl, nicosulfuron, oxasulfuron, primisulfuron, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron, orthosulfamuron, propyrisulfuron, flucetosulfuron, metazosulfuron, methiopyrsulfuron, monosulfuron-methyl, orsosulfuron, and iofensulfuron; imidazolinone-based such as imazapic, imazamethabenz, imazamox-ammonium, imazapyr, imazaquin, and imazethapyr; triazolopyrimidine sulfonamide-based such as cloransulam-methyl, diclosulam, florasulam, flumetsulam, metosulam, penoxsulam, pyroxsulam, metosulfam; pyrimidinyl(thio)benzoate-based such as bispyribac-sodium, pyribenzoxim, pyriftalid, pyrithiobac-sodium, pyriminobac-methyl, and pyrimisulfan; sulfonylaminocarbonyltriazolinone-based such as flucarbazone, propoxycarbazone, and thiencarbazone-methyl; sulfonanilide-based such as triafamone; and other ingredients considered to exhibit herbicidal effects by inhibiting the acetolactate synthase (ALS) (acetohydroxy acid synthase (AHAS)) of plants.

(c) Triazine-based such as ametryn, atrazine, cyanazine, desmetryne, dimethametryn, prometon, prometryn, propazine-based (propazine), CAT (simazine), simetryn, terbumeton, terbuthylazine, terbutryne, trietazine, atratone, and cybutryne; triazinone-based such as hexazinone, metamitron, and metribuzin; triazolinone-based such as amicarbazone; uracil-based such as bromacil, lenacil, and terbacil; pyridazinone-based such as PAC (chloridazon); carbamate-based such as desmedipham, phenmedipham, and swep; urea-based such as chlorobromuron, chlorotoluron, chloroxuron, dimefuron, DCMU (diuron), ethidimuron, fenuron, fluometuron, isoproturon, isouron, linuron, methabenzthiazuron, metobromuron, metoxuron, monolinuron, neburon, siduron, tebuthiuron, metobenzuron, and karbutilate; amide-based such as DCPA (propanil), and CMMP (pentanochlor); anilide-based such as cypromid; nitrile-based such as bromofenoxim, bromoxynil, and ioxynil; benzothiadiazinone-based such as bentazone; phenylpyridazin-based such as pyridate, and pyridafol; and other ingredients considered to exhibit herbicidal effects by inhibiting the photosynthesis of plants such as methazole.

(d) Bipyridylium-based such as diquat, and paraquat; and other ingredients considered to turn themselves into free radical in a plant body to produce reactive oxygen species and exhibit rapid herbicidal effects.

(e) Diphenylether-based such as acifluorfen-sodium, bifenox, chlomethoxynyl (chlomethoxyfen), fluoroglycofen, fomesafen, halosafen, lactofen, oxyfluorfen, nitrofen, and ethoxyfen-ethyl; phenylpyrazole-based such as fluazolate, and pyraflufen-ethyl; N-phenylphthalimide-based such as cinidon-ethyl, flumioxazin, flumiclorac-pentyl, and chlorphthalim; thiadiazole-based such as fluthiacet-methyl, and thidiazimin; oxadiazole-based such as oxadiazon, and oxadiargyl; triazolinone-based such as azafenidin, carfentrazone-ethyl, sulfentrazone, and bencarbazone; oxazolidinedione base such as pentoxazone; pyrimidinedione-based such as benzfendizone, and butafenacil; sulfonylamide-based such as saflufenacil; pyridazine-based such as flufenpyr-ethyl; and other ingredients considered to exhibit herbicidal effects by inhibiting the chlorophyll biosynthesis of plants and abnormally accumulating a photosensitizing peroxide substance in a plant body such as pyrachlonil, profluazol, tiafenacil, and trifludimoxazin.

(f) Pyridazinone-based such as norflurazon, and metflurazon; pyridinecarboxamide-based such as diflufenican, and picolinafen; triketone-based such as mesotrione, sulcotrione, tefuryltrione, tembotrione, bicyclopyrone, and fenquinotrione; isoxazole-based such as isoxachlortole, and isoxaflutole; pyrazole-based such as benzofenap, pyrazolate (pyrazolynate), pyrazoxyfen, topramezone, pyrasulfotole, and tolpyralate; triazole-based such as ATA (amitrol); isoxazolidinone-based such as clomazone; diphenylether-based such as aclonifen; and other ingredients considered to exhibit herbicidal effects by inhibiting the pigment biosynthesis of plants like carotenoid and have a whitening effect such as beflubutamid, fluridone, flurochloridone, flurtamone, benzobicyclone, methoxyphenone, and ketospiradox.

(g) Glycine-based such as glyphosate, glyphosate-ammonium, glyphosate-isopropylamine, and glyphosate trimesium (sulfosate); and other EPSP synthase inhibitors.

(h) Glutamine synthetase inhibitors like phosphinic acid-based such as glufosinate, glufosinate-ammonium, and bialaphos (bilanafos); and other ingredients considered to exhibit herbicidal effects by inhibiting amino acid biosynthesis of plants.

(i) Carbamate-based such as asulam; and other DHP (dihydropteroate) synthase inhibitors.

(j) Dinitroaniline-based such as bethrodine (benfluralin), butralin, dinitramine, ethalfluralin, oryzalin, pendimethalin, trifluralin, nitralin, and prodiamine; phosphoramidate base such as amiprofos-methyl, and butamifos; pyridine-based such as dithiopyr, and thiazopyr; benzamide-based such as propyzamide, and tebutam; benzoic acid-based such as chlorthal, and TCTP (chlorthal-dimethyl); carbamate-based such as IPC (chlorpropham), propham, carbetamide, and barban; arylalanine-based such as flamprop-M, and flamprop-M-isopropyl; chloracetamide-based such as acetochlor, alachlor, butachlor, dimethachlor, dimethenamid, dimethenamid-P, metazachlor, metolachlor, S-metolachlor, pethoxamid, pretilachlor, propachlor, propisochlor, and thenylchlor; acetamide-based such as diphenamid, napropamide, and naproanilide; oxyacetamido base such as flufenacet, and mefenacet; tetrazolinone-based such as fentrazamide; and other ingredients considered to exhibit herbicidal effects by inhibiting the microtubule polymerization, microtubule organization, and cell division of plants or by inhibiting the Very Long Chain Fatty Acid (VLCFA) biosynthesis such as anilofos, indanofan, cafenstrole, piperophos, methiozolin, fenoxasulfone, pyroxasulfone, and ipfencarbazone.

(k) Nitrile-based such as DBN (dichlobenil), and DCBN (chlorthiamid); benzamide-based such as isoxaben; triazolocarboxamide-based such as flupoxam; quinolinecarboxylic acid-based such as quinclorac; and other ingredients considered to exhibit herbicidal effects by inhibiting the cellulose synthesis such as triaziflam, and indaziflam.

(l) Dinitrophenol-based such as DNOC, DNBP (dinoseb), and dinoterb; and other ingredients considered to exhibit herbicidal effects by the uncoupling (membrane disruption).

(m) Thiocarbamate-based such as butylate, hexylthiocarbam (cycloate), dimepiperate, EPTC, esprocarb, molinate, orbencarb, pebulate, prosulfocarb, benthiocarb (thiobencarb), tiocarbazil, triallate, vernolate, and diallate; phosphorodithioate-based such as SAP (bensulide); benzofuran-based such as benfuresate, and ethofumesate; chlorocarbonic acid-based such as TCA, DPA (dalapon), and tetrapion (flupropanate); and other ingredients considered to exhibit herbicidal effects by inhibiting the lipid biosynthesis of plants.

(n) Phenoxycarboxylic acid-based such as clomeprop, 2,4-PA (2,4-D), 2,4-DB, dichlorprop, MCPA, MCPB, and MCPP (mecoprop); benzoic acid-based such as chloramben, MDBA (dicamba), and TCBA (2,3,6-TBA); pyridinecarboxylic acid-based such as clopyralid, aminopyralid, fluroxypyr, picloram, triclopyr, and halauxifen; quinolinecarboxylic acid-based such as quinclorac, and quinmerac; phthalamate semicarbazone-based such as NPA (naptalam), and diflufenzopyr; and other ingredients considered to exhibit herbicidal effects by disordering hormone actions of plants such as benazolin, diflufenzopyr, fluroxypyr, chlorflurenol, aminocyclopyrachlor, and DAS534.

(o) Arylaminopropionic acid-based such as flamprop-M-methyl/isopropyl; pyrazolium-based such as difenzoquat; organic arsenic base such as DSMA, and MSMA; and other herbicides such as bromobutide, chlorflurenol, cinmethylin, cumyluron, dazomet, daimuron, methyl-dymron, etobenzanid, fosamine, oxaziclomefone, oleic acid, pelargonic acid, pyributicarb, endothall, sodiumchlorate, metam, quinoclamine, cyclopyrimorate, tridiphane, and clacyfos.

2. Plant Growth Inhibiting Method

A plant growth inhibiting agent of the present invention, when applied to a place where a target plant germinates or grows, can inhibit the growth of the plant. In the present invention, target plants refer to problematic plants from the viewpoint of the landscape and safety, that is plants so-called weeds.

Examples of the target plant include weeds such as common amaranth, redroot pigweed, Indian lettuce, common thistle, beggar ticks, Carolina cranesbill, burr cucumber, flax-leaf fleabane, common evening primrose, Japanese knotweed, variableleaf yellowcress, creeping smartweed, thale cress, purple amaranth, black nightshade, water chickweed, toothed medick, spiked cudweed, Australian acalypha, Sumatran fleabane, birdeye speedwell, hydrocotyle ramiflora maxim, nodding spurge, Chinese plantain, oriental false hawksbeard, prickly sow-thistle, Indian goosegrass, sticky chickweed, creeping woodsorrel, asian flatsedge, vetch, Japanese dock, yellow nutsedge, cucumber herb, field penny-cress, Japanese yellow loosestrife, milk purslane, chickweed, Japanese false bindweed, white clover, common sorrel, bog yellowcress, field horsetail, hairy tare, annual bluegrass, sweet vernalgrass, common purslane, Canada goldenrod, dandelion, black bindweed, American false daisy, corn speedwell, Viola grypoceras, bitter cress, nipplewort, cogongrass, lawn pennywort, plantain leaf pussytoes, angel's trumpet, clover, sun spurge, spreeding sneezeweed, shepherdspurse, annual sowthistle, common groundsel, bog chickweed, shaggy soldier, Jersey cudweed, Philadelphia fleabane, nut grass, pink persicaria, purple deadnettle, kyllinga, daisy, sheep sorrel, horseweed, spotted catsear, ivyleaf speedwell, Indian strawberry, ribwort, henbit, prostrate knotweed, bird's-foot trefoil, violet wood-sorrel, *Sericea lespedeza*, southern crabgrass, broomsedge, Japanese clover, Japanese mugwort, and horsenettle.

An application place of a plant growth inhibiting agent of the present invention is not particularly limited, and may be a soil such as a garden, a park, a vacant lot, a road, and a riverbed, or a wetland along a side of a river, a lake, or a swamp.

As an application method, in consideration of the kind of a target plant and environmental conditions, a conventionally known method may be selected. A method may be a direct spray of a plant growth inhibiting agent of the present invention to stems and leaves of a target plant, a spray of the agent onto the surface of a soil, or a mixing of the agent with a soil. Further, a plant growth inhibiting agent of the present invention may be sprayed on the water surface of a wetland, or dissolved or dispersed in water of a wetland. Examples include a method in which a plant growth inhibiting agent of the present invention is sprayed on a soil in which weeds as described above are germinating. Furthermore, a plant growth inhibiting agent of the present invention is applied in advance to a place in which weeds are expected to germinate, whereby the emergence of weeds can be inhibited.

A used amount of a plant growth inhibiting agent of the present invention may be suitably determined in a range in which the characteristics of the compound (A) are not adversely affected in consideration of the kind of a compound to be the active ingredient, a content of the compound (A), a target plant, environmental conditions, and a dosage form used.

A plant growth inhibiting agent of the present invention is suitable for the application to a plant (stem and leaf spray), the application to a soil where a plant grows (soil application), the application to paddy water (water surface application), and the application to seeds (seed treatment). A plant growth inhibiting agent of the present invention can be used as diluted with water to a low concentration.

When used for the stem and leaf spray, the plant growth inhibiting agent diluted with water as described above is preferably sprayed in 10 to 300 L, and more preferably 10 to 100 L, per 10 ares.

When used for the soil application and the water surface application, the plant growth inhibiting agent diluted with water as described above is preferably sprayed, in terms of the ingredient (A), in 0.1 to 1000 g, and more preferably 10 to 100 g, per 10 ares.

3 Novel Compounds

Of the compounds represented by the above formula (I'), compounds represented by the following formula (III) or formula (IV) involve novel compounds.

[Compounds Represented by Formula (III)]

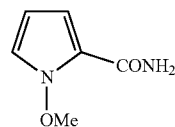

(III)

[Compounds Represented by Formula (IV)]

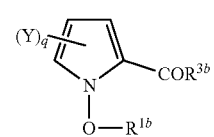

(IV)

Each of the substituents in the formula (IV) will be described below.

($R^{1b}$)

In the formula (IV), $R^{1b}$ represents a substituted or unsubstituted $C_2$ to $C_{20}$ alkyl group, a substituted or unsubstituted $C_6$ to $C_{14}$ aryl group, a substituted or unsubstituted 5- to 10-membered heteroaryl group, a substituted or unsubstituted $C_6$ to $C_{10}$ aryl $C_1$ to $C_6$ alkyl group, or a substituted or unsubstituted 5- to 10-membered heteroaryl $C_1$ to $C_6$ alkyl group.

Of these, $R^{1b}$ is preferably a substituted or unsubstituted $C_2$ to $C_{20}$ alkyl group, a substituted or unsubstituted $C_6$ to $C_{14}$ aryl group, or a substituted or unsubstituted $C_6$ to $C_{10}$ aryl $C_1$ to $C_6$ alkyl group, and more preferably a substituted or unsubstituted $C_2$ to $C_{20}$ alkyl group, or a substituted or unsubstituted $C_6$ to $C_{10}$ aryl $C_1$ to $C_6$ alkyl group.

The "$C_2$ to $C_{20}$ alkyl group" in "a substituted or unsubstituted $C_2$ to $C_{20}$ alkyl group" means a linear, branched, or cyclic alkyl group having 2 to 20 carbon atoms and includes an ethyl group, a propyl group, an isopropyl group, a butyl group, a cyclopropyl group, and a cyclopropylmethyl group.

The $C_2$ to $C_{20}$ alkyl group has preferably 3 or more carbon atoms. Further, such a group has preferably 12 or less carbon atoms.

Furthermore, the $C_2$ to $C_{20}$ alkyl group is preferably linear.

Examples of the substituent substitutable with a $C_2$ to $C_{20}$ alkyl group include a halogen atom, a hydroxyl group, a $C_1$ to $C_6$ alkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, and a cyano group, but not limited thereto. Further, the substituent may have one or more same or different substituents.

Examples of the halogen atom include a fluoro group, a chloro group, a bromo group, and an iodo group.

Examples of the $C_1$ to $C_6$ alkoxy group include a methoxy group, an ethoxy group, a n-propoxy group, an i-propoxy group, a n-butoxy group, a s-butoxy group, an i-butoxy group, and a t-butoxy group.

Examples of the $C_6$ to $C_{10}$ aryl group include a phenyl group, and a naphthyl group.

Examples of the 5- to 6-membered heteroaryl group include a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; and a 6-membered heteroaryl group such as a pyridyl group, a pyrazinyl group, a pyrimidinyl group, a pyridazinyl group, and a triazinyl group.

Examples of the $C_6$ to $C_{10}$ aryloxy group include a phenoxy group, and a naphthoxy group.

Examples of the substituent substitutable on a $C_6$ to $C_{10}$ aryl group, a 5- to 6-membered heteroaryl group, or a $C_6$ to $C_{10}$ aryloxy group include a $C_1$ to $C_6$ alkyl group such as a methyl group, an ethyl group, a n-propyl group, an i-propyl group, a n-butyl group, a s-butyl group, an i-butyl group, a t-butyl group, a n-pentyl group, and a n-hexyl group; a hydroxyl group; a $C_1$ to $C_6$ alkoxy group such as a methoxy group, an ethoxy group, a n-propoxy group, an i-propoxy group, a n-butoxy group, a s-butoxy group, an i-butoxy group, and a t-butoxy group; a halogeno group such as a fluoro group, a chloro group, a bromo group, and an iodo group; a $C_1$ to $C_6$ haloalkyl group such as a chloromethyl group, a chloroethyl group, a trifluoromethyl group, a 1,2-dichloro-n-propyl group, a 1-fluoro-n-butyl group, and a perfluoro-n-pentyl group; a $C_1$ to $C_6$ haloalkoxy group such as a trifluoromethoxy group, a 2-chloro-n-propoxy group, and a 2,3-dichlorobutoxy group; a cyano group; and a nitro group.

The "$C_6$ to $C_{14}$ aryl group" in "a substituted or unsubstituted $C_6$ to $C_{14}$ aryl group" means an aromatic hydrocarbon ring wherein the number of carbon atoms constituting the ring is 6 to 14, and may be monocyclic or polycyclic.

Examples of the $C_6$ to $C_{14}$ aryl group include a phenyl group, a naphthyl group, an anthracenyl group, and a phenanthrenyl group, and one of preferable $C_6$ to $C_{14}$ aryl groups includes a phenyl group.

Examples of the substituent substitutable for a $C_6$ to $C_{14}$ aryl group include a halogen atom, a $C_1$ to $C_6$ alkyl group, a $C_1$ to $C_6$ haloalkyl group, a hydroxyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those respectively exemplified in "the substituent substitutable for a $C_2$ to $C_{20}$ alkyl group".

Examples of the $C_1$ to $C_6$ alkyl group include a methyl group, an ethyl group, a n-propyl group, an i-propyl group, a n-butyl group, a s-butyl group, an i-butyl group, a t-butyl group, a n-pentyl group, and a n-hexyl group.

Examples of the $C_1$ to $C_6$ haloalkyl group include a chloromethyl group, a chloroethyl group, a trifluoromethyl group, a 1,2-dichloro-n-propyl group, a 1-fluoro-n-butyl group, and a perfluoro-n-pentyl group.

Examples of the $C_1$ to $C_6$ haloalkoxy group include a trifluoromethoxy group, a 2-chloro-n-propoxy group, and a 2,3-dichlorobutoxy group.

The "5- to 10-membered heteroaryl group" in "a substituted or unsubstituted 5- to 10-membered heteroaryl group" means an aromatic ring which includes, as a ring constituent element, one or more hetero atoms selected from the group consisting of an oxygen atom, a sulfur atom, and a nitrogen atom, and may be monocyclic or polycyclic.

Examples of the 5- to 10-membered heteroaryl group include a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; a 6-membered heteroaryl group such as a pyridyl group, a pyrazinyl group, a pyrimidinyl group, a pyridazinyl group, and a triazinyl group; a 9-membered heteroaryl group such as an indolyl group, a benzofuranyl group, a benzothienyl group, a benzoxazolyl group, and a benzothiazolyl group; a 10-membered heteroaryl group such as a quinolinyl group, an isoquinolinyl group, and quinoxalinyl group.

Examples of the substituent substitutable for a 5- to 10-membered heteroaryl group include a halogen atom, a $C_1$ to $C_6$ alkyl group, a $C_1$ to $C_6$ haloalkyl group, a hydroxyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, and a cyano group, but not limited thereto. Further, the substituent may have one or more same or different substituents.

Specific examples of the halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those exemplified respectively in "the substituent substitutable for a $C_2$ to $C_{20}$ alkyl group".

Specific examples of the above $C_1$ to $C_6$ alkyl group, $C_1$ to $C_6$ haloalkyl group, and $C_1$ to $C_6$ haloalkoxy group include the same substituents as those exemplified respectively in "the substituent substitutable for a $C_6$ to $C_{14}$ aryl group".

"Substituted or unsubstituted $C_6$ to $C_{10}$ aryl $C_1$ to $C_6$ alkyl group"

A "$C_6$ to $C_{10}$ aryl $C_1$ to $C_6$ alkyl group" is an alkyl group substituted with one or more aryl groups.

Examples of the $C_6$ to $C_{10}$ aryl $C_1$ to $C_6$ alkyl group include a benzyl group, a phenylethyl group, a naphthylmethyl group, and a naphthylethyl group. One of preferable $C_6$ to $C_{10}$ aryl $C_1$ to $C_6$ alkyl groups is a benzyl group.

Examples of the substituent substitutable for a $C_6$ to $C_{10}$ aryl $C_1$ to $C_6$ alkyl group include a halogen atom, a $C_1$ to $C_6$ alkyl group, a $C_1$ to $C_6$ haloalkyl group, a hydroxyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those exemplified respectively in "the substituent substitutable for a $C_2$ to $C_{20}$ alkyl group."

Specific examples of the above $C_1$ to $C_6$ alkyl group, $C_1$ to $C_6$ haloalkyl group, and $C_1$ to $C_6$ haloalkoxy group include the same substituents as those exemplified respectively in "the substituent substitutable for a $C_6$ to $C_{14}$ aryl group."

The "5- to 10-membered heteroaryl $C_1$ to $C_6$ alkyl group" in "a substituted or unsubstituted 5- to 10-membered heteroaryl $C_1$ to $C_6$ alkyl group" is an alkyl group substituted with one or more heteroaryl groups.

Examples of the 5- to 10-membered heteroaryl $C_1$ to $C_6$ alkyl group include a furylmethyl group, a pyridylmethyl group, and a pyridylethyl group.

Examples of the substituent substitutable for a 5- to 10-membered heteroaryl $C_1$ to $C_6$ alkyl group include a halogen atom, a $C_1$ to $C_6$ alkyl group, a $C_1$ to $C_6$ haloalkyl group, a hydroxyl group, a $C_1$ to $C_6$ alkoxy group, a $C_1$ to $C_6$ haloalkoxy group, a substituted or unsubstituted $C_6$ to $C_{10}$ aryl group, a substituted or unsubstituted 5- to 10-membered heteroaryl group, a substituted or unsubstituted $C_6$ to $C_{10}$ aryloxy group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those respectively exemplified in "the substituent substitutable for a $C_2$ to $C_{20}$ alkyl group."

Specific examples of the above $C_1$ to $C_6$ alkyl group, $C_1$ to $C_6$ haloalkyl group, and $C_1$ to $C_6$ haloalkoxy group include the same substituents as those respectively exemplified in "the substituent substitutable for a $C_6$ to $C_{14}$ aryl group."

($R^{3b}$)

In the formula (IV), $R^{3b}$ represents OH, a substituted or unsubstituted $C_1$ to $C_6$ alkoxy group, or a group represented by a formula: $N(R^4)_2$ (wherein $R^4$ represents a hydrogen atom or a substituted or unsubstituted $C_1$ to $C_6$ alkyl group, and two $R^4$ may bond to form a divalent organic group).

The "$C_1$ to $C_6$ alkoxy group" in "a substituted or unsubstituted $C_1$ to $C_6$ alkoxy group" means a linear, branched, or cyclic alkoxy group having 1 to 6 carbon atoms and includes a methoxy group, an ethoxy group, a propoxy group, an isopropoxy group, and a butoxy group.

Examples of the substituent substitutable for a $C_1$ to $C_6$ alkoxy group include a halogen atom, a $C_1$ to $C_6$ alkoxy group, a substituted or unsubstituted $C_6$ to $C_{10}$ aryl group, a substituted or unsubstituted 5- to 6-membered heteroaryl group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group include the same substituents as those respectively exemplified in "the substituent substitutable for a $C_2$ to $C_{20}$ alkyl group."

The $R^4$ in "a group represented by a formula: $N(R^4)_2$" represents a hydrogen atom or a substituted or unsubstituted $C_1$ to $C_6$ alkyl group.

The "$C_1$ to $C_6$ alkyl group" means a linear, branched, or cyclic alkyl group having 1 to 6 carbon atoms and includes a methyl group, and an ethyl group.

Examples of the substituent substitutable for a $C_1$ to $C_6$ alkyl group include a halogen atom, a $C_1$ to $C_6$ alkoxy group, a substituted or unsubstituted $C_6$ to $C_{10}$ aryl group, a substituted or unsubstituted 5- to 6-membered heteroaryl group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, and substituted or unsubstituted 5- to 6-membered heteroaryl group include the same substituents as those respectively exemplified in "the substituent substitutable for a $C_1$ to $C_{20}$ alkyl group."

Examples of the divalent organic group formed by two $R^4$ bonding include a $C_2$ to $C_5$ alkylene group such as a dimethylene group, a trimethylene group, a tetramethylene group, and a pentamethylene group, and a $C_2$ to $C_3$ alkyleneoxy $C_2$ to $C_3$ alkylene group such as a dimethyleneoxydimethylene group.

(Y, q)

In the formula (IV), Y represents a substituent, and q represents any integer of 0 to 3.

Examples of the substituent include a halogen atom, a $C_1$ to $C_6$ alkyl group, a $C_1$ to $C_6$ haloalkyl group, a hydroxyl group, a $C_1$ to $C_6$ alkoxy group, a substituted or unsubstituted $C_6$ to $C_{10}$ aryl group, a substituted or unsubstituted 5- to 6-membered heteroaryl group, a substituted or unsubstituted $C_6$ to $C_{10}$ aryloxy group, and a cyano group, but not limited thereto. Further, the substituent may have one or more same or different substituents.

Specific examples of the above halogen atom, $C_1$ to $C_6$ alkoxy group, substituted or unsubstituted $C_6$ to $C_{10}$ aryl group, substituted or unsubstituted 5- to 6-membered heteroaryl group, and $C_6$ to $C_{10}$ aryloxy group include the same substituents as those respectively exemplified in "the substituent substitutable for a $C_2$ to $C_{20}$ alkyl group."

Specific examples of the above $C_1$ to $C_6$ alkyl group, and $C_1$ to $C_6$ haloalkyl group include the same substituents as those respectively exemplified in "the substituent substitutable for a $C_6$ to $C_{14}$ aryl group."

(Synthetic Method)

The compounds represented by the above formula (III) or formula (IV) can be synthesized by a known method, for example, by the following method.

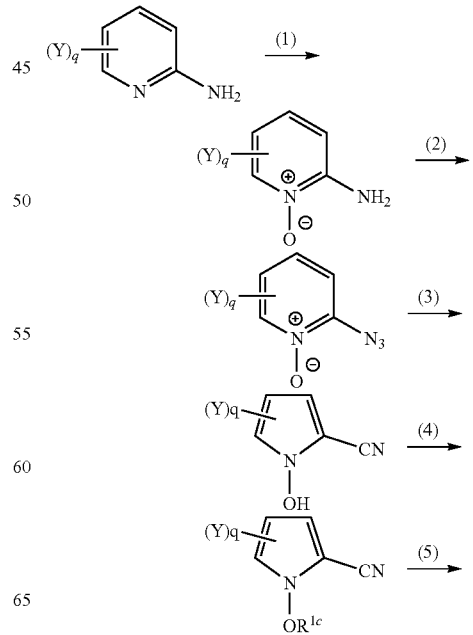

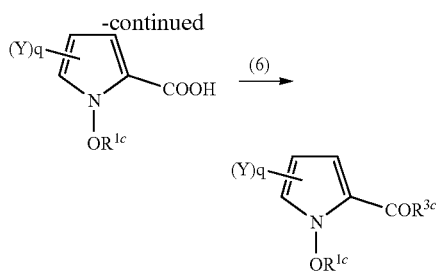

In the above reaction formula, Y and q are each defined as in the formula (IV). $R^{1c}$ is a methyl group or defined as $R^{1b}$ in the formula (IV). $R^{3c}$ is a group wherein an OH group is excluded from the definition of $R^{3b}$ in the formula (IV).

In the above reaction formula, a preparation method of N-hydroxy-2-cyanopyrrole, which is an important production intermediate, will be described.

N-Hydroxy-2-cyanopyrrole can be prepared by a heat transfer reaction of 2-azidopyridine N-oxide. For example, a method described in European Journal of Organic Chemistry, Volume 2004, Issue 21, 4492-4502 can be used as a reference.

Reaction (1) Oxidation of the N Atom in a Pyridine Ring

The N atom in a pyridine ring can be oxidized quantitatively by oxidation using mCPBA. The reaction is preferably carried out in a chloroform solvent at 0° C. to room temperature.

Reaction (2) Azidation of an Amino Group

For azidation of an amino group, after diazotization of the amino group, a substitution reaction with a metal azide can be used. 2-Aminopyridine N-oxide, after converted to hydrochloride at a low temperature, is diazotized by reacting with sodium nitrite. After diazotization, an aqueous solution of a metal azide is carefully added dropwise to obtain 2-azidopyridine N-oxide.

Reaction (3) Conversion of the Pyridine Ring to a Pyrrole Ring

Thermolysis of the 2-azidopyridine N-oxide in a benzene solvent causes elimination of nitrogen and a ring-opening reaction, and 2-cyano-1-hydroxypyrrole can be obtained as a result of the subsequent re-cyclization reaction.

A reaction solvent used is preferably aromatic hydrocarbon such as benzene and xylene, and heating is preferably carried out under reflux or in a sealed tube.

Note that step (4) (conversion of an OH group to an $OR_{1a}$ group), step (5) (conversion of a cyano group to a carboxyl group), and step (6) (esterification or amidation of the carboxyl group) are routine method and the explanations are left out, but can be carried out by, for example, the methods described in examples.

EXAMPLES

Hereinafter, the present invention will be described more specifically in reference with examples, but the present invention is not limited thereto.

In the synthesis of the compounds of the following Example 1 to Example 7 and Comparative Example 1, all reactions were observed using thin-layer chromatography. (Merck 60 F254 precoated silica gel plates (0.25 mm thickness)). 1H and 13C NMR were observed using JASCO Corporation ECX 500 FT-NMR nuclear magnetic resonance apparatus. ESIMS was measured using Shimadzu Corporation LCMS-2020. Kanto Kagaku silica gel 60N was used for the column chromatography for purification, and Merck 60 F254 precoated silica gel plates (0.25 mm thickness) was used for preparative thin-layer chromatography.

Example 1

1-Methoxy-1H-pyrrole-2-carboxylic acid (compound (6a)) was synthesized according to the following scheme.

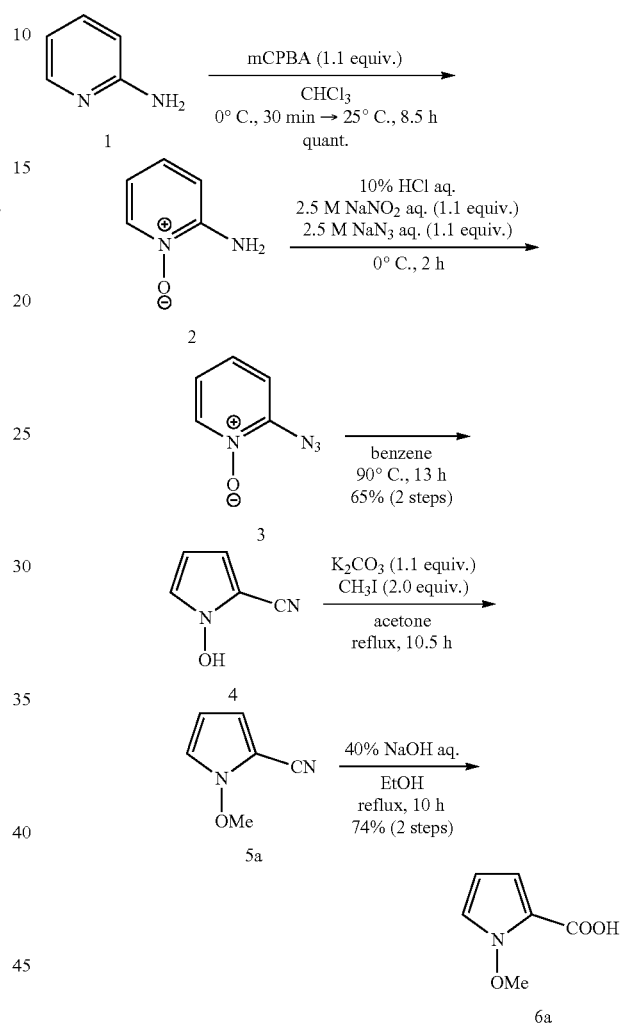

(I-1) Synthesis of 2-aminopyridine 1-oxide (Compound (2))

3-Chloroperbenzoic acid (mCPBA, 5.6 g, 24 mmol) was added to a solution of 2-aminopyridine (compound (1), 2.0 g, 22 mmol) in chloroform (220 mL) cooled to 0 degrees. The reaction mixture was stirred for 30 minutes at a reaction temperature of 0 degrees, followed by elevating the temperature to room temperature and stirring for 8.5 hours. An organic solvent was evaporated under reduced pressure from the reaction mixture. The obtained crude product was purified by silica gel column chromatography (eluent: 25% methanol/ethyl acetate) to obtain quantitatively (2.5 g) the desired 2-aminopyridine 1-oxide (compound (2)) in the form of an orange solid.

Physical Property Data $^1$H-NMR (500 MHz, CDCl$_3$) δ 8.10 (d, J=6.5 Hz, 1H), 7.13 (t, J=8.0 Hz, 1H), 6.76 (d, J=4.3 Hz, 1H), 6.64 (t, J=3.5

Hz, 1H), 5.62 (br s, 2H); $^{13}$C-NMR (125 MHz, CDCl$_3$) δ 150.3, 137.9, 128.4, 113.7, 109.8; ESI-MS m/z 111 [M+H]$^+$ (II-1) Synthesis of 2-azidopyridine 1-oxide (Compound (3))

A 2.5 M sodium nitrite aqueous solution (800 μL) was carefully added to an aqueous solution of the compound (2) (200 mg, 1.8 mmol) in 10% hydrochloric acid (6.0 mL) cooled to 0 degrees, and stirred for 30 minutes. To this solution, an aqueous solution of 2.5 M sodium azide (800 μL) was carefully added, and stirred for 2 hours. The reaction mixture was transferred to a separatory funnel, and extracted 8 times with chloroform (10 mL). The combined organic (chloroform) layers were dried over by adding a suitable amount of magnesium sulfate, and then magnesium sulfate was removed by filtration. An organic solvent was evaporated under reduced pressure from the dried organic layer to obtain a crude product (compound (3)). In addition, the obtained crude product (compound (3)) was directly used for the subsequent reaction.

(III-1) Synthesis of 1-hydroxy-1H-pyrrole-2-carbonitrile (Compound (4))

Under an argon atmosphere, a solution of the crude product (compound (3)) obtained in the above (II-1) in benzene (4.5 mL) was stirred at 90 degrees for 13 hours using a shield tube. An organic solvent was evaporated under reduced pressure from the reaction mixture. The obtained crude product was purified by silica gel column chromatography (eluent: 10% ethyl acetate/n-hexane→20% ethyl acetate/n-hexane) to obtain the desired 1-hydroxy-1H-pyrrole-2-carbonitrile (compound (4)) in the form of a light brown oil with a 2-step yield of 65% (128 mg).
Physical Property Data
$^1$H-NMR (500 MHz, CDCl$_3$) δ 6.97 (dd, J=2.0, 2.8 Hz, 1H), 6.62 (dd, J=2.0, 4.8 Hz, 1H), 6.02 (dd, J=2.8, 5.3 Hz, 1H); $^{13}$C-NMR (125 MHz, CDCl$_3$) δ 123.4, 116.3, 112.7, 105.5, 100.4; ESI-MS m/z 107 [M−H]$^-$ (IV-1) Synthesis of 1-methoxy-1H-pyrrole-2-carbonitrile (Compound (5a))

Under an argon atmosphere, potassium carbonate (140 mg, 1.0 mmol) and iodomethane (110 μL, 1.8 mmol) were added to a solution of the compound (4) (98 mg, 0.91 mmol) in acetone (3.9 mL). The reaction mixture was stirred at 90 degrees for 10.5 hours. The reaction mixture was cooled to room temperature, followed by removing solid substances in the reaction system by filtration. At this operation, the reaction mixture was eluted by washing the residue with acetone. An organic solvent was evaporated under reduced pressure from the collected filtrate, and the residue was transferred to a separatory funnel, and extracted 3 times with diethyl ether (10 mL). The combined organic (diethyl ether) layers were dried over by adding a suitable amount of magnesium sulfate, and then magnesium sulfate was removed by filtration. An organic solvent was evaporated under reduced pressure from the dried organic layer to obtain a crude product (compound (5a)). In addition the obtained crude product (compound (5a)) was directly used for the subsequent reaction.

(V-1) Synthesis of 1-methoxy-1H-pyrrole-2-carboxylic acid (Compound (6a))

A 40% sodium hydroxide aqueous solution (1.2 mL) was added to a solution of the crude product (compound (5a)) obtained in the above (IV-1) in ethanol (1.9 mL). The reaction mixture was stirred at 110 degrees for 10 hours, and after cooling the reaction mixture to room temperature, an organic solvent was evaporated under reduced pressure from the reaction mixture. A suitable amount of water was added thereto, followed by adjusting pH of the solution to pH 3 using a 50% phosphoric acid aqueous solution. The resultant was transferred to a separatory funnel, and extracted 3 times using chloroform (10 mL). The combined organic (chloroform) layers were dried over by adding a suitable amount of magnesium sulfate, and then magnesium sulfate was removed by filtration. An organic solvent was evaporated under reduced pressure from the dried organic layer. The obtained crude product was purified by silica gel column chromatography (eluent: chloroform→5% methanol/chloroform) to obtain the desired 1-methoxy-1H-pyrrole-2-carboxylic acid (compound (6a)) in the form of a light brown solid with a 2-step yield of 74% (104 mg).
Physical Property Data
$^1$H-NMR (500 MHz, CDCl$_3$) δ 7.06-7.04 (m, 1H), 6.91-6.90 (m, 1H), 6.07-6.05 (m, 1H), 4.12 (s, 3H); $^{13}$C-NMR (125 MHz, CDCl$_3$) δ 164.5, 123.5, 117.3, 116.1, 105.0, 67.9; ESI-MS m/z 140 [M−H]$^-$ Example 2

1-Methoxy-1H-pyrrole-2-carboxamide (compound (7)) was synthesized according to the following scheme.

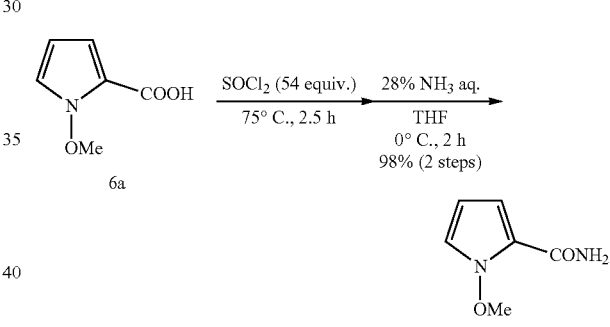

(I-2) Synthesis of Compound (6a)

Compound (6a) was obtained in the same manner as in Example 1.

(II-2) Synthesis of 1-methoxy-1H-pyrrole-2-carboxamide (Compound (7))

Under an argon atmosphere, thionyl chloride (1.4 mL, 1.9 mmol) was added to the compound (6a) (50 mg, 0.35 mmol). The reaction mixture was stirred at 75 degree for 2.5 hours, and after cooling the reaction mixture to room temperature, thiony chloride was evaporated under reduced pressure from the reaction mixture. Dehydrated tetrahydrofuran (THF, 2.0 mL) was added to the obtained crude product, and after the reaction mixture was cooled to 0 degrees, 28% aqueous ammonia (3.9 mL) was carefully added thereto. The reaction mixture was stirred at 0 degrees for 2 hours, and the organic solvent was evaporated under reduced pressure from the reaction mixture. Chloroform (10 mL) was added to the obtained crude product to be dissolved, the resultant was transferred to a separatory funnel, aqueous ammonia (10 mL) was added, and an organic layer was separated. This operation was repeated 3 times in total. The combined organic (chloroform) layers were dried over by adding a suitable amount of magnesium sulfate, and then magnesium sulfate was removed by filtration. An organic solvent was evaporated under reduced pressure from the dried organic layer. The obtained crude product was purified by silica gel column chromatography (eluent: 3% methanol/chloroform) to obtain the desired 1-methoxy-1H-pyrrole 2-carboximide (compound (7)) in the form of a yellow brown oil with a 2-step yield of 98% (49 mg).

Physical Property Data $^1$H-NMR (500 MHz, CDCl$_3$) δ 6.93 (t, J=1.3 Hz, 1H), 6.76 (dd, J=1.8, 4.3 Hz, 1H), 6.05 (t, J=1.9 Hz, 1H), 4.08 (s, 3H); $^{13}$C-NMR (125 MHz, CDCl$_3$) δ 161.1, 121.0, 119.9, 112.2, 105.0, 68.3; ESI-MS m/z 141 [M+H]$^+$ Example 3

1-Ethoxy-1H-pyrrole-2-carboxylic acid (compound (6b)) was synthesized according to the following scheme.

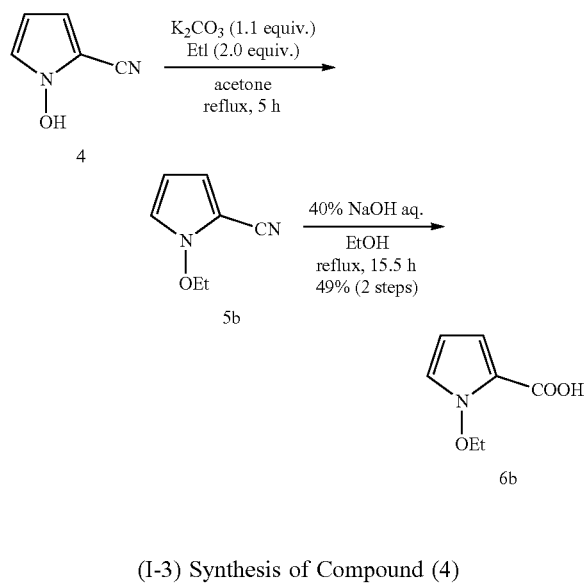

(I-3) Synthesis of Compound (4)

Compound (4) was obtained in the same manner as in (I-1) to (III-1) of Example 1.

(II-3) Synthesis of 1-ethoxy-1H-pyrrole-2-carbonitrile (Compound (5b))

Under an argon atmosphere, potassium carbonate (14 mg, 0.1 mmol) and iodoethane (15 μL, 0.19 mmol) were added to a solution of the compound (4) (10 mg, 93 μmol) in acetone (400 μL). The reaction mixture was stirred at 70 degrees for 5 hours. The reaction mixture was cooled to room temperature, followed by removing solid substances in the reaction system by filtration. At this operation, the reaction mixture was eluted by washing the residue with acetone. An organic solvent was evaporated under reduced pressure from the collected filtrate, the residue was transferred to a separatory funnel, and extracted 3 times with diethyl ether (10 mL). The combined organic (diethyl ether) layers were dried over by adding a suitable amount of magnesium sulfate, and then magnesium sulfate was removed by filtration. An organic solvent was evaporated under reduced pressure from the dried organic layer to obtain a crude product (compound (5b)). In addition, the obtained crude product (compound (5b)) was directly used for the subsequent reaction.

(III-3) Synthesis of 1-ethoxy-1H-pyrrole-2-carboxylic acid (Compound (6b))

A 40% sodium hydroxide aqueous solution (130 μL) was added to a solution of the crude product (compound (5b) obtained in the above (II-3) in ethanol (200 μL). The reaction mixture was stirred at 110 degrees for 15.5 hours, and after cooling the reaction mixture to room temperature, an organic solvent was evaporated under reduced pressure from the reaction mixture. A suitable amount of water was added thereto, followed by adjusting pH of the solution to pH 3 with a 50% phosphoric acid aqueous solution. The resultant was transferred to a separatory funnel, and extracted 3 times with chloroform (10 mL). The combined organic (chloroform) layers were dried over by adding a suitable amount of magnesium sulfate, and then magnesium sulfate was removed by filtration. An organic solvent was evaporated under reduced pressure from the dried organic layer. The obtained crude product was purified by thin-layer chromatography (eluent: 5% methanol/chloroform) to obtain desired 1-ethoxy-1H-pyrrole-2-carboxylic acid (compound (6b)) in the form of a brown solid with a 2-step yield of 49% (7.0 mg).

Physical Property Data $^1$H-NMR (500 MHz, CDCl$_3$) δ 7.02 (t, J=2.5 Hz, 1H), 6.91 (dd, J=1.3, 2.3 Hz, 1H), 6.04 (dd, J=2.8, 2.4 Hz, 1H), 4.33 (q, J=7.2 Hz, 2H), 1.37 (t, J=7.0 Hz, 3H); $^{13}$C-NMR (125 MHz, CDCl$_3$) δ 164.3, 124.3, 117.6, 116.0, 104.8, 76.4, 13.5; ESI-MS m/z 156 [M+H]$^+$, 154 [M−H]$^−$ Example 4

1-Propoxy-1H-pyrrole-2-carboxylic acid (compound (6d)) was synthesized according to the following scheme.

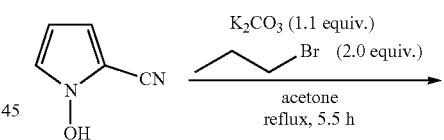

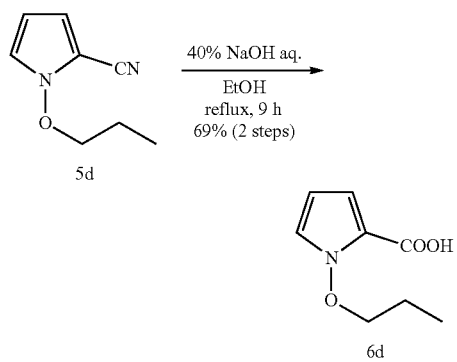

(I-4) Synthesis of Compound (4)

Compound (4) was obtained in the same manner as in (I-1) to (III-1) of Example 1.

(II-4) Synthesis of 1-propoxy-1H-pyrrole-2-carbonitrile (Compound (5d))

Under an argon atmosphere, potassium carbonate (70 mg, 0.51 mmol) and 1-bromopropane (84 μL, 0.93 mmol) were added to a solution of the compound (4) (50 mg, 0.46 mol) in acetone (2.0 mL). The reaction mixture liquid was stirred at 70 degrees for 5.5 hours. The reaction mixture was cooled to room temperature, followed by removing solid substances in the reaction system by filtration. At this operation, the reaction mixture was extracted by washing the residue with acetone. An organic solvent was evaporated under reduced pressure from the collected filtrate, the residue was transferred to a separatory funnel, and extracted 3 times with diethyl ether (10 mL). The combined organic (diethyl ether) layers were dried over by adding a suitable amount of magnesium sulfate, and then magnesium sulfate was removed by filtration. An organic solvent was evaporated under reduced pressure from the dried organic layer to obtain a crude product (compound (5d)). The obtained crude product (compound (5d)) was directly used for the subsequent reaction.

(III-4) Synthesis of 1-propoxy-1H-pyrrole-2-carboxylic Acid (Compound (6d))

A 40% sodium hydroxide aqueous solution (630 μL) was added to a solution of the crude product (compound (5d)) obtained in the above (II-4) in ethanol (980 μL). The reaction mixture was stirred at 110 degrees for 9 hours, and after cooling the reaction mixture to room temperature, an organic solvent was evaporated under reduced pressure from the reaction mixture. A suitable amount of water was added thereto, followed by adjusting pH of the solution to pH 3 with a 50% phosphoric acid aqueous solution. The resultant was transferred to a separatory funnel, and extracted 3 times with chloroform (10 mL). The combined organic (chloroform) layers were dried over by adding a suitable amount of magnesium sulfate, and then magnesium sulfate was removed by filtration. An organic solvent was evaporated under reduced pressure from the dried organic layer. The obtained crude product was purified by silica gel chromatography (eluent: 1% methanol/chloroform) to obtain desired 1-propoxy-1H-pyrrole 2-carboxylic acid (compound (6d)) in the form of a brown solid with a 2-step yield of 69% (54 mg).

Physical Property Data $^1$H-NMR (500 MHz, CDCl$_3$) δ 7.02-7.01 (m, 1H), 6.92 (dd, J=2.5, 2.3 Hz, 1H), 6.05-6.03 (m, 1H), 4.22 (t, J=6.8 Hz, 2H), 1.79 (sext, J=7.1 Hz, 2H), 1.05 (t, J=7.5 Hz, 3H); $^{13}$C-NMR (125 MHz, CDCl$_3$) δ 164.6, 124.2, 117.6, 116.0, 104.8, 82.2, 21.4, 10.3; ESI-MS m/z 170 [M+H]$^+$, 168 [M−H]$^−$

Example 5

1-Isopropoxy-1H-pyrrole-2-carboxylic acid (compound (6e)) was synthesized according to the following scheme.

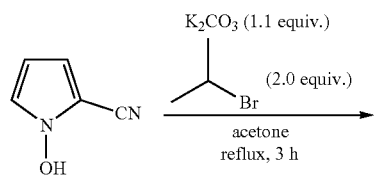

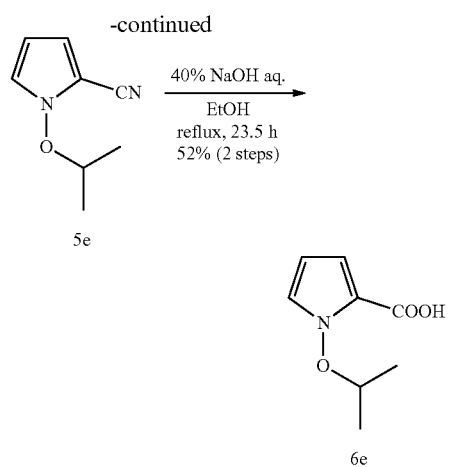

(I-5) Synthesis of Compound (4)

Compound (4) was obtained in the same manner as in (I-1) to (III-1) of Example 1

(II-5) Synthesis of 1-isopropoxy-1H-pyrrole-2-carbonitrile (Compound (5e))

Under an argon atmosphere, potassium carbonate (100 mg, 0.75 mmol) and 2-bromopropane (130 μL, 1.4 mmol) were added to a solution of the compound (4) (74 mg, 0.68 mol) in acetone (3.0 mL). The reaction mixture was stirred at 70 degrees for 3 hours. The reaction mixture was cooled to room temperature, followed by removing solid substances in the reaction system by filtration. At this operation, the reaction mixture was eluted by washing the residue with acetone. An organic solvent was evaporated under reduced pressure from the collected filtrate, the residue was transferred to a separatory funnel, and extracted 3 times with diethyl ether (10 mL). The combined organic (diethyl ether) layers were dried over by adding a suitable amount of magnesium sulfate, and then magnesium sulfate was removed by filtration. An organic solvent was evaporated under reduced pressure from the dried organic layer to obtain a crude product (compound (5e)). In addition, the obtained crude product (compound (5e)) was directly used for the subsequent reaction.

(III-5) Synthesis of 1-isopropoxy-1H-pyrrole-2-carboxylic Acid (Compound (6e))

A 40% sodium hydroxide aqueous solution (940 μL) was added to a solution of the crude product (compound (5e)) obtained in the above (II-5) in ethanol (1.5 mL). The reaction mixture liquid was stirred at 110 degrees for 23.5 hours, and after cooling the reaction mixture to room temperature, an organic solvent was evaporated under reduced pressure from the reaction mixture. A suitable amount of water was added thereto, followed by adjusting pH of the solution to pH 3 with a 50% phosphoric acid aqueous solution. The resultant was transferred to a separatory funnel, and extracted 3 times with chloroform (10 mL). The combined organic (chloroform) layers were dried over by adding a suitable amount of magnesium sulfate, and then magnesium sulfate was removed by filtration. An organic solvent evaporated under reduced pressure from the dried organic layer. The obtained crude product was purified by silica gel chromatography (eluent: 1% methanol/chloroform) to obtain desired 1-isopropoxy-1H-pyrrole-2-carboxylic acid (compound (6e)) in the form of a brown solid with a 2-step yield of 52% (60 mg)).

Physical Property Data $^1$H-NMR (500 MHz, CDCl$_3$) δ 6.97 (t, J=2.8 Hz, 1H), 6.93 (dd, J=2.0, 4.5 Hz, 1H), 6.03 (dd, J=2.8, 4.8 Hz, 1H), 4.58 (sept, J=6.2 Hz, 1H), 1.32 (d, J=3.0 Hz, 6H); $^{13}$C-NMR (125 MHz, CDCl$_3$) δ 164.4, 125.6, 117.9, 116.2, 104.4, 82.0, 20.5; ESI-MS m/z 170 [M+H]$^+$, 168 [M–H]$^-$ Example 6

1-Butoxy-1H-pyrrole-2-carboxylic acid (compound (6f)) was synthesized according to the following scheme.

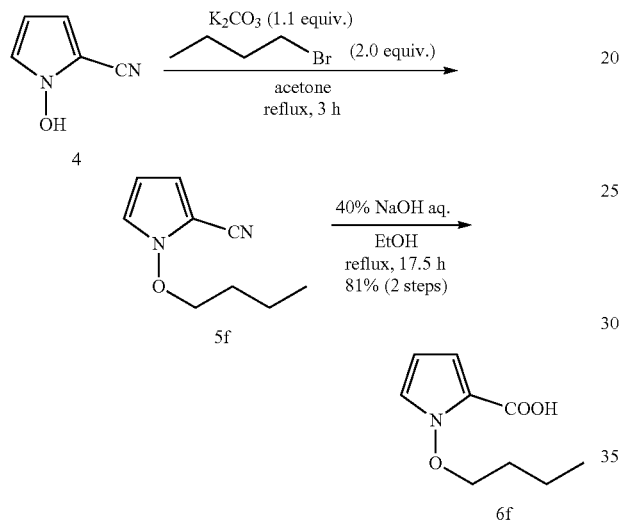

(I-6) Synthesis of Compound (4)

Compound (4) was obtained in the same manner as in (I-1) to (III-1) of Example 1.

(II-6) Synthesis of 1-butoxy-1H-pyrrole-2-carbonitrile (Compound (5f))

Under an argon atmosphere, potassium carbonate (56 mg, 0.41 mmol) and 1-bromobutane (79 μL, 0.74 mmol) were added to a solution of the compound (4) (40 mg, 0.37 mmol) in acetone (1.6 mL). The reaction mixture was stirred at 70 degrees for 3 hours. The reaction mixture was cooled to room temperature, followed by removing solid substances in the reaction system by filtration. At this operation, the reaction mixture was eluted by washing the residue with acetone. An organic solvent was evaporated under reduced pressure from the collected filtrate, the residue was transferred to a separatory funnel, and extracted 3 times with diethyl ether (10 mL). The combined organic (diethyl ether) layers were dried over by adding a suitable amount of magnesium sulfate, and then magnesium sulfate was removed by filtration. An organic solvent was evaporated under reduced pressure from the dried organic layer to obtain a crude product (compound (5f)). In addition, the obtained crude product (compound (5f)) was directly used for the subsequent reaction.

(III-6) Synthesis of 1-butoxy-1H-pyrrole-2-carboxylic Acid (Compound (6f))

A 40% sodium hydroxide aqueous solution (510 μL) was added to a solution of the crude product (compound (5f)) obtained in the above (II-6) in ethanol (790 μL). The reaction mixture was stirred at 110 degrees for 17.5 hours, and after cooling the reaction mixture to room temperature, an organic solvent was evaporated under reduced pressure from the reaction mixture. A suitable amount of water was added thereto, followed by adjusting pH of the solution to pH 3 with a 50% phosphoric acid aqueous solution. The resultant was transferred to a separatory funnel, and extracted 3 times with chloroform (10 mL). The combined organic (chloroform) layers were dried over by adding a suitable amount of magnesium sulfate, and then magnesium sulfate was removed by filtration. An organic solvent was evaporated under reduced pressure from the dried organic layer. The obtained crude product was purified by silica gel chromatography (eluent: 1% methanol/chloroform) to obtain desired 1-butoxy-1H-pyrrole-2-carboxylic acid (compound (6f)) in the form of a light brown solid with a 2-step yield of 81% (55 mg).

Physical Property Data $^1$H-NMR (500 MHz, CDCl$_3$) δ 7.02-7.01 (m, 1H), 6.93-6.91 (m, 1H), 6.05-6.04 (m, 1H), 4.27 (t, J=6.8 Hz, 2H), 1.75 (quint, J=7.1 Hz, 2H), 1.50 (sext, J=7.4 Hz, 2H), 0.98 (t, J=7.5 Hz, 3H); $^{13}$C-NMR (125 MHz, CDCl$_3$) δ 164.5, 124.2, 117.6, 116.0, 104.8, 80.6, 30.1, 19.0, 14.0; ESI-MS m/z 184 [M+H]$^+$, 182 [M–H]$^-$ Example 7

1-(Benzyloxy)-1H-pyrrole-2-carboxylic acid (compound (6g)) was synthesized according to the following scheme.

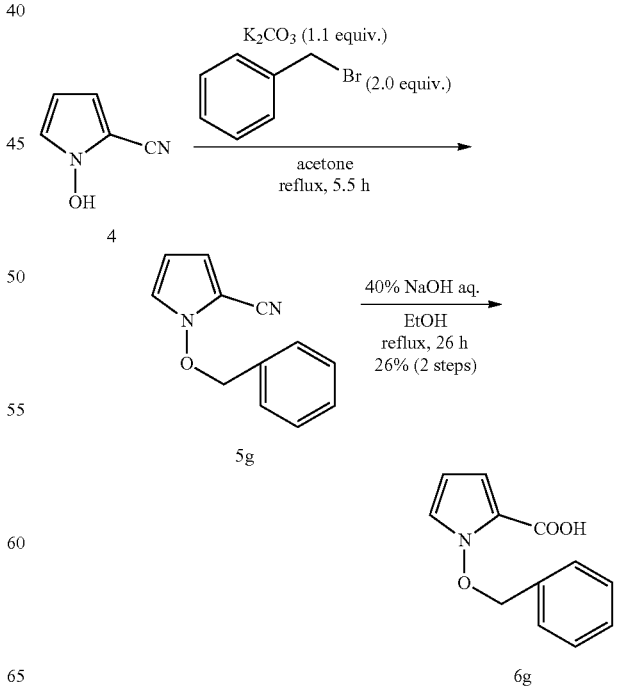

(I-7) Synthesis of Compound (4)

Compound (4) was obtained in the same manner as in (I-1) to (III-1) of Example 1.

(II-7) Synthesis of 1-(benzyloxy)-1H-pyrrole-2-carbonitrile (Compound (5g))

Under an argon atmosphere, potassium carbonate (28 mg, 0.20 mmol) and benzyl bromide (44 μL, 0.37 mmol) were added to a solution of the compound (4) (20 mg, 0.19 mmol) in acetone (800 μL). The reaction mixture was stirred at 70 degrees for 5.5 hours. The reaction mixture was cooled to room temperature, followed by removing solid substances in the reaction system by filtration. At this operation, the reaction mixture was eluted by washing the residue with acetone. An organic solvent was evaporated under reduced pressure from the collected filtrate, the residue was transferred to a separatory funnel, and extracted 3 times with diethyl ether (10 mL). The combined organic (diethyl ether) layers were dried over by adding a suitable amount of magnesium sulfate, and then magnesium sulfate was removed by filtration. An organic solvent was evaporated under reduced pressure from the dried organic layer to obtain a crude compound (compound (5g)). In addition, the obtained crude product (compound (5g)) was directly used for the subsequent reaction.

(III-7) Synthesis of 1-(benzyloxy)-1H-pyrrole-2-carboxylic Acid (Compound (6g))

A 40% sodium hydroxide aqueous solution (260 μL) was added to a solution of the crude product (compound (5g)) obtained in the above (II-7) in ethanol (400 μL). The reaction mixture was stirred at 110 degrees for 20 hours, and after cooling the reaction mixture to room temperature, an organic solvent was evaporated under reduced pressure from the reaction mixture. A suitable amount of water was added thereto, followed by adjusting pH of the solution to pH 3 with a 50% phosphoric acid aqueous solution. The resultant was transferred to a separatory funnel, and extracted 3 times with chloroform (10 mL). The combined organic (chloroform) layers were dried over by adding a suitable amount of magnesium sulfate, and then magnesium sulfate was removed by filtration. An organic solvent was evaporated under reduced pressure from the dried organic layer. The obtained crude product was purified by silica gel chromatography (eluent: 1% methanol/chloroform→5% methanol/chloroform) to obtain desired 1-(benzyloxy)-1H-pyrrole-2-carboxylic acid (compound (6g)) in the form of a brown solid with a 2-step yield of 26% (11 mg).

Physical Property Data $^1$H-NMR (500 MHz, CDCl$_3$) δ 7.42-7.40 (m, 5H), 6.96 (s, 1H), 6.75 (s, 1H), 5.97 (s, 1H), 5.25 (s, 2H); $^{13}$C-NMR (125 MHz, CDCl$_3$) δ 164.4, 134.1, 130.3, 130.1, 129.4, 128.8, 128.6, 124.9, 117.5, 116.3, 104.6, 82.3; ESI-MS m/z 218 [M+H]$^+$, 216 [M−H]$^−$

Comparative Example 1

1-Hydroxy-1H-pyrrole-2-carboxylic acid (compound (6c)) was synthesized according to the following scheme.

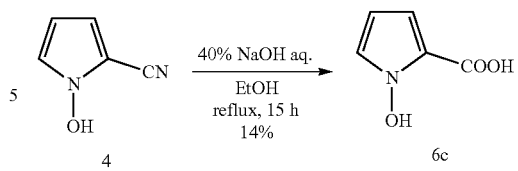

(I-8) Synthesis of Compound (4)

Compound (4) was obtained in the same manner as in (I-1) to (III-1) of Example 1.

(II-8) Synthesis of 1-hydroxy-1H-pyrrole-2-carboxylic Acid (Compound (6c))

A 40% sodium hydroxide aqueous solution (130 μL) was added to a solution of the compound (4) (9.7 mg, 93 μmol) in ethanol (200 μL). The reaction mixture was stirred at 110 degrees for 15 hours, and after cooling the reaction mixture to room temperature, an organic solvent was evaporated under reduced pressure from the reaction mixture. A suitable amount of water was added thereto, followed by adjusting pH of the solution to pH 3 with a 50% phosphoric acid aqueous solution. The resultant was transferred to a separatory funnel, and extracted 3 times using chloroform (10 mL). The combined organic (chloroform) layers were dried over by adding a suitable amount of magnesium sulfate, and then magnesium sulfate was removed by filtration. An organic solvent was evaporated under reduced pressure from the dried organic layer. The obtained crude product was purified by thin-layer chromatography (eluent: 20% methanol/chloroform) to obtain desired 1-hydroxy-1H-pyrrole-2-carboxylic acid (compound (6c)) in the form of a light brown solid with a 2-step yield of 14% (1.6 mg).

Physical Property Data $^1$H-NMR (500 MHz, CDCl$_3$) δ 7.06 (s, 1H), 6.82 (s, 1H), 6.06 (s, 1H); ESI-MS m/z 126 [M−H]$^−$

Example 8

The following compounds were synthesized by the same method as above.

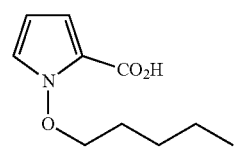

Physical Property Data $^1$H-NMR (500 MHz, CDCl$_3$) δ 7.02 (t, J=2.8 Hz, 1H), 6.92 (dd, J=2.5, 2.8 Hz, 1H), 6.04 (dd, J=2.8, 4.8 Hz, 1H), 4.26 (t, J=7.0 Hz, 2H), 1.77 (quin, J=7.0 Hz, 2H), 1.48-1.36 (m, 4H), 0.94 (t, J=7.0 Hz, 3H); $^{13}$C-NMR (125 MHz, CDCl$_3$) δ 164.6, 124.2, 117.6, 116.0, 104.8, 80.9, 27.9, 27.7, 22.6, 14.1

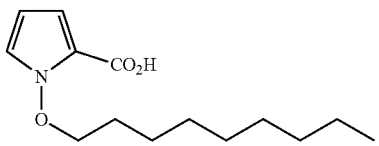
(8b)

Physical Property Data
$^1$H-NMR (500 MHz, CDCl$_3$) δ 7.01 (t, J=2.3 Hz, 1H), 6.92 (dd, J=2.3, 4.8 Hz, 1H), 6.04 (q, J=2.3 Hz, 1H), 4.25 (t, J=6.8 Hz, 2H), 1.76 (quin, J=7.1 Hz, 2H), 1.46 (quin, J=7.4 Hz, 2H), 1.36-1.23 (m, 10H), 0.89 (t, J=7.0 Hz, 3H); $^{13}$C-NMR (125 MHz, CDCl$_3$) δ 164.5, 124.1, 117.7, 115.9, 104.7, 80.9, 32.0, 29.6, 29.5, 29.4, 28.0, 25.8, 22.8, 14.2

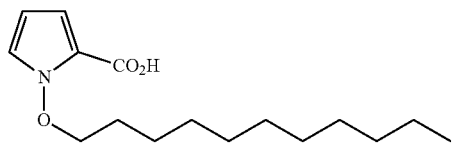
(8c)

Physical Property Data
$^1$H-NMR (500 MHz, CDCl$_3$) δ 7.01 (d, J=1.5 Hz, 1H), 6.92 (t, J=2.5 Hz, 1H), 6.04 (dd, J=1.5, 2.8 Hz, 1H), 4.26 (t, J=5.5 Hz, 2H), 1.76 (quin, J=6.6 Hz, 2H), 1.46 (t, J=6.5 Hz, 2H), 1.28 (s, 14H), 0.89 (t, J=6.0 Hz, 3H); $^{13}$C-NMR (125 MHz, CDCl$_3$) δ 164.7, 124.1, 117.6, 116.0, 104.7, 80.8, 32.0, 29.7, 29.6, 29.5, 29.5, 28.0, 25.8, 22.8, 14.2

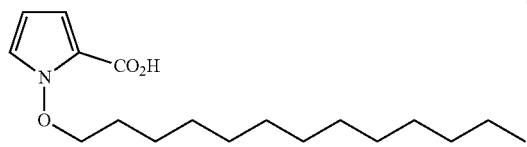
(8d)

Physical Property Data
$^1$H-NMR (500 MHz, CDCl$_3$) δ 7.01 (t, J=2.3 Hz, 1H), 6.92 (dd, J=1.8, 4.3 Hz, 1H), 6.04 (dd, J=2.5, 4.0 Hz, 1H), 4.26 (t, J=6.5 Hz, 2H), 1.76 (quin, J=7.1 Hz, 2H), 1.46 (quin, J=7.3 Hz, 2H), 1.27 (s, 18H), 0.89 (t, J=6.8 Hz, 3H); $^{13}$C-NMR (125 MHz, CDCl$_3$) δ 164.6, 124.2, 117.6, 116.0, 104.7, 80.9, 32.1, 29.8-29.5 (7C), 28.0, 25.8, 22.8, 14.2; ESI-MS m/z 289 [M–H]$^-$

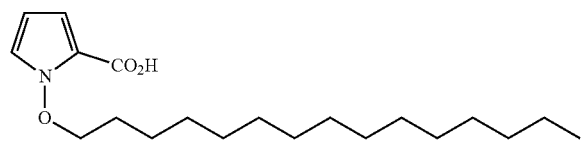
(8e)

Physical Property Data
$^1$H-NMR (500 MHz, CDCl$_3$) δ 7.01 (t, J=2.5 Hz, 1H), 6.91 (dd, J=2.5, 4.5 Hz, 1H), 6.04 (dd, J=3.0, 4.5 Hz, 1H), 4.25 (t, J=6.5 Hz, 2H), 1.76 (quin, J=7.1 Hz, 2H), 1.45 (quin, J=7.3 Hz, 2H), 1.31-1.26 (m, 22H), 0.88 (t, J=7.0 Hz, 3H); $^{13}$C-NMR (125 MHz, CDCl$_3$) δ 163.7, 124.1, 117.5, 115.9, 104.8, 81.0, 32.1, 29.9-29.5 (9C), 28.0, 25.8, 22.8, 14.3

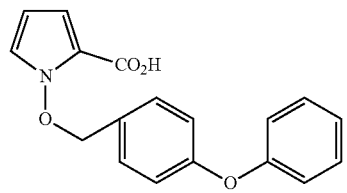
(8f)

Physical Property Data
$^1$H-NMR (500 MHz, CDCl$_3$) δ 7.39-7.34 (m, 4H), 7.14 (t, J=7.3 Hz, 1H), 7.03 (dd, J=8.3, 12.3 Hz, 4H), 6.97 (dd, J=2.0, 4.5 Hz, 1H), 6.81 (t, J=2.5 Hz, 1H), 6.00 (dd, J=2.5, 4.0 Hz, 1H), 5.22 (s, 2H); $^{13}$C-NMR (125 MHz, CDCl$_3$) 164.6, 158.5, 156.8, 131.8, 130.0, 128.6, 124.9, 123.8, 119.4, 118.7, 117.5, 116.3, 104.7, 81.8

(8g)

Physical Property Data
$^1$H-NMR (500 MHz, CDCl$_3$) δ 7.34 (d, J=8.5 Hz, 2H), 6.96 (dd, J=1.8, 4.8 Hz, 1H), 6.90 (d, J=8.5 Hz, 2H), 6.73 (t, J=2.5 Hz, 1H), 5.96 (dd, J=3.0 Hz, 1H), 5.19 (s, 2H), 3.82 (s, 3H); $^{13}$C-NMR (125 MHz, CDCl$_3$) δ 164.5, 160.5, 131.7, 126.2, 125.0, 117.5, 116.2, 114.1, 104.5, 81.9, 55.4

(8h)

Physical Property Data
$^1$H-NMR (500 MHz, CDCl$_3$) δ 7.88-7.82 (m, 4H), 7.59 (d, J=8.0 Hz, 1H), 7.51 (quin, J=6.5 Hz, 2H), 6.93 (dd, J=1.3, 4.3 Hz, 1H), 6.72 (t, J=2.3 Hz, 1H), 5.93 (dd, J=3.0, 4.5 Hz, 1H), 5.41 (s, 2H); $^{13}$C-NMR (125 MHz, CDCl$_3$) δ 163.4, 133.7, 133.2, 132.2, 131.6, 129.7, 128.7, 128.3, 127.9, 127.1, 126.8, 126.5, 124.9, 116.1, 104.6, 82.4; ESI-MS m/z 266 [M–H]$^-$ (8i)

Physical Property Data
$^1$H-NMR (400 MHz, CDCl$_3$) δ 2.0-2.1 (m, 2H), 2.3-2.45 (m, 2H), 4.33 (t, 2H), 6.05-6.07 (m, 1H), 6.61-6.62 (m, 1H), 6.94-6.95 (m, 1H).

[Evaluation 1] Activities on Plants
[Evaluation 1-1]

The compound (6a) synthesized in Example 1 was evaluated for the activities on plants. The evaluation was carried out according to the following procedures (1-1) to (1-3).

(1-1) Preparation of a Plant Growth Medium

Mixed salts for Murashige and Skoog medium (NIHON PHARMACEUTICAL CO., LTD.), 1% (w/v) sucrose, and 0.05% (w/v) MES were mixed, and pH of the solution was adjusted to pH 5.7 with potassium hydroxide. 1.5% (w/v) Agar was added to the mixed solution, and the solution was sterilized at 120° C. in an autoclave for 20 minutes. The test compound (compound (6a)) and DMSO for a control experiment, were added at this stage and blended. In addition, the compound (6a) was used at the indicated concentrations to the concentrations shown in FIG. 1. Fifty ml each of the medium was dispensed in sterile No. 2 square petri dishes (Eiken Chemical Co., Ltd.) to prepare agar medium.

(1-2) Growth of a Plant

As a plant material, Col-0, which is a wild-type strain of thale cress, was used.

Seeds, after their surfaces were sterilized, were planted on the agar medium, and vernalized at 4° C. for 16 hours. Growth of the plant was carried out in a growth chamber (SANYO MLR-351) under the conditions of an illuminance of 3 at 23° C. with constant light. The agar medium was allowed to stand upright in the chamber to grow the plant for 7 days.

(1-3) Evaluation

Lids of the petri dishes used for the test were opened, the test results were recorded with a scanner, and with the scanned images, The results are shown in FIG. 1. As shown in FIG. 1, when the compound (6a) was added, epidermal cells of the roots were twisted leftward and abnormality in a direction of root growth was observed. Further, the effect of plant growth inhibition was significantly observed as concentrations of the compound (6a) to be increased.

Further, FIG. 2 shows observation photos by a stereomicroscope. The observation with the stereomicroscope was carried out with all the root tips pointing downward. Under the condition wherein the compound (6a) was added, epidermal cells of the roots were observed to have been twisted leftward.

[Evaluation 1-2]

The compound (7) synthesized in Example 2 was evaluated in the same manner as in Evaluation 1-1. The results are shown in FIG. 3. As shown in FIG. 3, when the compound (7) was added, epidermal cells of the roots were twisted leftward and abnormality in a direction of the root growth was observed.

[Evaluation 1-3]

The compound (6b) synthesized in Example 3 was evaluated in the same manner as in Evaluation 1-1. The results are shown in FIG. 4. As shown in FIG. 4, when the compound (6b) was added, epidermal cells of the roots were twisted leftward and abnormality in a direction of the root growth was observed.

[Evaluation 1-4] to [Evaluation 1-7]

The compounds synthesized in Examples 4 to 7 (compounds (6d) to (6g)) were evaluated in the same manner as in Evaluation 1-1. The results are shown in FIG. 5 to FIG. 8. As shown in FIG. 5 to FIG. 8, when the compound (6d) to the compound (6g) were added, abnormality in a direction of the root growth were observed, growth inhibition were observed. No germinations were observed when each of the compound (6d) and the compound (6e) was added at a concentration of 1000 µM. Further, substantially no germination was observed when the compound (6f) was added even at a concentration of 500 µM, and no germination was observed when the compound (6f) was added at a concentration of 1000µ. When the compound (6g) was added, a plant growth inhibiting effect was observed even more than when each of the compounds (6d) to (6f). was added.

[Evaluation 1-8]

The compound (6c) synthesized in Comparative Example 1 was evaluated in the same manner as in Evaluation 1-1. The results are shown in FIG. 9. As shown in FIG. 9, no activity was observed when the comparative compound (6c) was added.

[Evaluation 1-9]

As positive controls, Propyzamide and oryzalin, were evaluated in the same manner as in Evaluation 1-1. The results are shown in FIG. 10. As shown in FIG. 10, abnormality in a direction of the root growth was also observed even under the condition wherein propyzamide and oryzalin were added.

Further, the compound (6a) of Example 1 and the compound (7) of Example 2 were evaluated for activities on animal cells in [Evaluation 2] to [Evaluation 5]. In addition, the 50% ethanol (50% EtOH) used for the evaluation means 50% volume/volume ethanol, which is an aqueous ethanol solution in a 50% concentration obtained by diluting 100% anhydrous ethanol with an equivalent amount of water. 50% Ethanol is a solvent in which the compound (6a) or the compound (7) was dissolved, and used as a control to observe the affect of the solvent on the cell proliferation.

[Evaluation 2] Evaluation for a Cell Proliferation Inhibiting Activity on Human Cultured Cancer Cells (HeLa Cell)

The compound (6a) of Example 1 and the compound (7) of Example 2 were evaluated for a cell proliferation inhibiting activity on human cultured cancer cells (HeLa cell).

HeLa cells were cultured in a 96-well plate for 32 hours under the culture conditions of 5% carbon dioxide and at 37° C. by adding the compound (6a) or the compound (7) (final concentration 200 µM), 50% ethanol (final concentration 1%), or staurosporine (final concentration 1 µM) to Dulbecco's Modified Eagle's Medium (DMEM). Every 8 hours after the culture was started, living cell counts were measured with a cell counting kit (DOJINDO LABORATORIES).

In addition, staurosporine was used as a control of the compound which inhibits the cell proliferation.

The results are shown in FIG. 11. In addition, the result shown as No-Treat in the figure is the result when where nothing was added to Dulbecco's Modified Eagle's Medium (DMEM).

As shown in FIG. 11, staurosporine induced the apoptosis. On the other hand, the compound (6a) and the compound (7) had no affect at all in 200 µM, thereby confirming that these compounds do not affect the growth rate of human cultured cells (HeLa cell).

[Evaluation 3] Evaluation for Growth Inhibiting Activity on *Schizosaccharomyces pombe*

The compound (6a) or the compound (7) was evaluated for the growth inhibiting activity on *Schizosaccharomyces pombe*.

The compound (6a) or the compound (7) (final concentration 100 µM) or 50% ethanol (final concentration 0.5%) was added to YE medium in which *Schizosaccharomyces pombe* (wild-type strain 972) was inoculated to carry out shaking culture at 30° C. Six, 12, 18, 24, and 30 hours after the culture was started, turbidity (OD600) of the culture medium was measured with a spectrophotometer to analyze the affect of the compound (6a) or the compound (7), or 50% ethanol on the growth of the *Schizosaccharomyces pombe* cells.

The results are shown in FIG. 12. In addition, the result shown as No-Treat in the figure is the result when nothing was added to YE medium in which *Schizosaccharomyces pombe* (wild-type strain 972) was inoculated.

As shown in FIG. 12, it was observed that neither the compound (6a) nor the compound (7) inhibits the growth of *Schizosaccharomyces pombe*. In addition, 50% ethanol was similarly observed not to inhibit the growth of *Schizosaccharomyces pombe*.

[Evaluation 4] Evaluation for Growth Inhibiting Activity on *Saccharomyces cerevisiae*

The compound (6a) or the compound (7) was evaluated for growth inhibiting activity on *Saccharomyces cerevisiae*.

The compound (6a) or the compound (7) (final concentration 10 μM or 100 μM), or 50% ethanol (final concentration 0.05% or 0.5%) was added to YPD medium in which *Saccharomyces cerevisiae* (BY4741 strain) was inoculated to carry out shaking culture at 30° C. Four, 8, 16, and 24 hours after the culture was started, turbidity (OD600) of the culture medium was measured with a spectrophotometer to analyze the affect of the compound (6a) or the compound (7), or 50% ethanol on the growth of the *Schizosaccharomyces cerevisiae* cells.

The results are shown in FIG. 13. In addition, the result shown as No-Treat in the figure is the result when nothing was added to YPD medium in which *Saccharomyces cerevisiae* (BY4741 strain) was inoculated.

As shown in FIG. 13, it was observed that neither the compound (6a) nor the compound (7) inhibits the growth of *Schizosaccharomyces pombe*. In addition, 50% ethanol was similarly observed not to inhibit the growth of *Schizosaccharomyces cerevisiae*.

[Evaluation 5] Evaluation for *E. coli* Growth Inhibiting Activity

The compound (6a) or the compound (7) was evaluated for *E. coli* growth inhibiting activity.

The compound (6a) or the compound (7) (final concentration 10 μM or 100 μM), 50% ethanol (final concentration 0.05% or 0.5%), or ampicillin (final concentration 50 μg/ml) was added to LB medium in which *E. coli* (DH5a strain) was added to carry out shaking culture at 37° C. One, 2, 4, and 6 hours after the culture was started, turbidity (OD600) of the culture medium was measured with a spectrophotometer to analyze the affect of the compound (6a) or the compound (7), 50% ethanol, ampicillin on the growth of *E. coli* cells.

In addition, ampicillin was used as a control of the compound which inhibits the growth.

The results are show in FIG. 14. In addition, the result shown as No-Treat in the figure is the result when nothing was added to LB medium in which *E. coli* (DH5a strain) was inoculated.

As shown in FIG. 14, *E. coli* growth inhibition was observed when the control ampicillin was added, but it was observed that neither the compound (6a) nor the compound (7) inhibits the *E. coli* growth. In addition, 50% ethanol was similarly observed not to inhibit the growth of *E. coli*.

As shown in FIG. 11 to FIG. 14 in the above, the compound (6a) of Example 1 and the compound (7) of Example 2 were observed not to inhibit the cell proliferation of animal cells while having the growth inhibiting activity on plants.

[Evaluation 6] Activities on Plants

The compounds (8a) to (8h) were evaluated in the same manner as in Evaluation 1-1. The results are shown in FIG. 15 to FIG. 22. In addition, each of addition concentration of the compounds was 50 μM. All of the compounds were observed to have a plant growth inhibiting effect.

[Evaluation 7] Evaluation for Cytotoxicity on Human Cultured Cancer Cells (HeLa Cell)

The compound (8b) and the compound (8f) were evaluated for cytotoxicity on human cultured cancer cells (HeLa cell).

HeLa cells were cultured in a 96-well plate using Dulbecco's Modified Eagle's Medium (DHEM) under the culture conditions of 5% carbon dioxide and at 37° C. The compound (8b) (final concentration 50 μM), the compound (8f) (final concentration 50 μM), DMSO (final concentration 0.25%), Actinomycin D (final concentration 5 μg/ml) or Nocodazole (final concentration 100 ng/ml) was added 0 (48-hr compound treated sample), 12 (36-hr compound treated sample), 24 (24-hr compound treated sample), 36 (12-hr compound treated sample), and 48 (0-hr compound treated sample) hours after the culture was started. All of the samples were measured for living cell counts 48 hours after the culture was started with a cell counting kit (DOJINDO LABORATORIES), and a measured value of each-time compound treated-sample was divided by the measured value of 0-time compound treated sample to calculate a relative survival rate.

In addition, a transcription inhibitor Actinomycin D and a tubulin polymerization inhibitor Nocodazole were used as controls of the compounds which had cytotoxicity (induces apoptosis). DMSO is a solvent in which the compound (8b) or the compound (8f) was dissolved, and used as a control to observe the affect of the solvent on the cells.

The results are shown in FIG. 23. Actinomycin D and Nocodazole induced apoptosis, but the compound (8b) and the compound (8f) were observed not to affect the viability of the human cultured cancer cells (HeLa cell).

[Evaluation 8] Activities on Plants

The compound (8b), the compound (8f), and the compound (8i) were evaluated by the following method.

(8-1) Preparation of Plant Growth Medium 0.44% (w/v) Mixed salts for Murashige and Skoog medium (SIGMA), 1% (w/v) sucrose, and 0.05% (w/v) MES were mixed, and pH of the solution was adjusted to pH 5.7 with potassium hydroxide. 1.5% (w/v) Agar was added to the mixture, which was sterilized at 120° C. in an autoclave for 20 minutes. The test compound and dimethylformamide containing 1.5% of polyoxyethylenesorbitan monolaurate for a control experiment, were added at this stage and blended. In addition, the compound was used by adjusting an addition concentration to 200 μM. Four ml each of the medium was dispensed in sterile glass test tube (NICHIDEN RIKA GLASS CO., LTD.) to prepare agar medium.

(8-2) Growth of Plants

As a plant material, Col-0, which is a wild-type strain of thale cress, was used.

Seeds, after their surfaces were sterilized, were planted on the agar medium, and the growth of the plant was carried out in a plant incubator (CFH-405) under the conditions of an illuminance of 3 at 23° C. with constant light. The plants on the agar medium were grown for 8 days in the chamber.

(8-3) Evaluation

The plant growth inhibition effect of the compounds was evaluated by conversion to indexes according to the following investigation criteria.

Indexes on the plant growth inhibition effects
0: No effect
1: Growth of the root part was inhibited 50% or less compared with non-treated area.
2: Growth of the root part was inhibited 50% or more compared with non-treated area.
3: Growth of the root part was substantially inhibited.
4: Germination was inhibited.

As a result of the test, the compound (8b) indicated an index "4". The compound (8f) indicated an index "3", and the compound (8i) indicated an index "2."

Further, the compounds of the present invention were synthesized by the method described below.

Example 9

1-Pentyloxy-4-phenyl-1H-pyrrole-2-carboxylic acid (compound (9a)) was synthesized according to the following scheme.

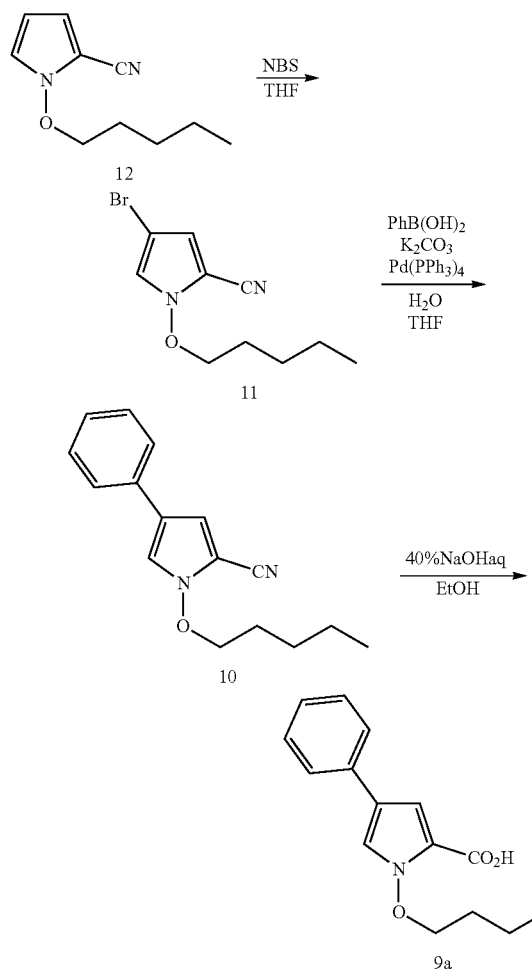

0.82 g (4.6 mmol) of 1-pentyloxy-1H-pyrrole-2-carbonitrile (compound 12) was dissolved in 20 mL of THF. 0.86 g (4.83 mmol) of N-bromosuccinimide was added to this solution and stirred at room temperature for 2 hours.

An organic solvent was evaporated under reduced pressure, and the residue was purified by silica gel chromatography (eluent; hexane:ethyl acetate=9:1 (v/v)) to obtain 4-bromo-1-pentyloxy-1H-pyrrole-2-carbonitrile (compound 11) (1.05 g, yield 89%).

0.26 g (1.0 mmol) of the obtained 4-bromo-1-pentyloxy-1H-pyrrole-2-carbonitrile was dissolved in 5 mL of THF, and phenylboronic acid (0.13 g; 1.1 mmol), potassium carbonate (0.15 g; 1.1 mmol), Pd(PPh$_3$)$_4$ (0.13 g; 0.11 mmol), and 5 mL of distilled water were sequentially added and the solution was heated under reflux for 7 hours.

The reaction mixture was cooled to room temperature, added to water, and extracted twice with ethyl acetate. The obtained organic layers were washed with saturated brine, and subsequently dried over anhydrous magnesium sulfate. The resultant was concentrated under reduced pressure, and the obtained crude product was purified by silica gel column chromatography (eluate; hexane:ethyl acetate=9:1 (v/v)) to obtain 1-pentyloxy-4-phenyl-1H-pyrrole-2-carbonitrile (compound 10) (0.14 g, yield 55%).

The obtained 1-pentyloxy-4-pheny-1H-pyrrole-2-carbonitrile (0.13 g; 0.51 mmol) was dissolved in 2 mL of ethanol, 1 mL of a 40% sodium hydroxide aqueous solution was added, and the reaction mixture was stirred for 24 hours.

The reaction mixture was cooled to room temperature, subsequently pH of which was adjusted to pH 3 with concentrated hydrochloric acid, and extracted twice with ethyl acetate. The obtained organic layer was washed with saturated brine, and subsequently dried over anhydrous magnesium sulfate. The resultant was concentrated under reduced pressure, and the obtained crude product was purified by silica gel column chromatography (eluate; chloroform:methanol=9:1 (v/v)) to obtain desired 1-pentyloxy-4-phenyl-1H-pyrrole-2-carboxylic acid (compound (9a)) (0.067 g, yield 48%).

A melting point of the obtained compound (9a) was 97 to 98° C.

The compounds shown in the following Table 1 were synthesized by the same method as above.

In addition, in the table Me represents a methyl group, $^n$Pen represents a n-pentyl group, $^n$Non represents a n-nonyl group, and Bn represents a benzyl group. Physical property values of the obtained compounds are also shown. With regard to the compounds with * in the physical property value column, NMR data are shown.

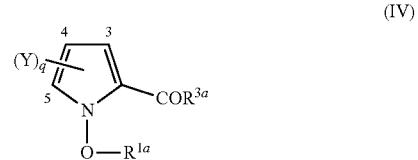
(IV)

TABLE 1

| Compound No. | (Y)$_q$ | R$^{3a}$ | R$^{1a}$ | Physical property value |
|---|---|---|---|---|
| 9b | 4-Cl | OH | $^n$Non | m.p. 76-79° C. |
| 9c | 4-Me | OH | $^n$Non | m.p. 58-59° C. |
| 9d | — | NHMe | $^n$Non | * |
| 9e | — | NHBn | $^n$Non | * |
| 9f | — | NHCH$_2$CF$_3$ | $^n$Non | * |
| 9g | — | NMe$_2$ | $^n$Non | * |
| 9h | — | Morpholin-4-yl | $^n$Non | * |
| 9i | 4-(Pyridin-3-yl) | OH | $^n$Pen | * |
| 9j | 4-(Thiophen-3-yl) | OH | $^n$Pen | m.p. 127-129° C. |
| 9k | — | OEt | $^n$Non | * |

9d

¹H-NMR (400 MHz, CDCl₃) δ0.86 (t, 3H), 1.15-1.45 (m, 12H), 1.65-1.80 (m, 2H), 2.95 (d, 3H), 4.17 (t, 2H), 5.98-6.00 (m, 1H), 6.6-6.75 (m, 2H), 6.82-6.83 (m, 1H).

9e

¹H-NMR (400 MHz, CDCl₃) δ0.88 (t, 3H), 1.15-1.35 (m, 12H), 1.45-1.6 (m, 2H), 4.10 (t, 2H), 4.60 (d, 2H), 6.00-6.03 (m, 1H), 6.74-6.77 (m, 1H), 6.83-6.84 (m, 1H), 7.03 (bs, 1H), 7.2-7.35 (m, 5H).

9f

¹H-NMR (400 MHz, CDCl₃) δ0.87 (t, 3H), 1.15-1.45 (m, 12H), 1.65-1.8 (m, 2H), 4.05-4.15 (m, 2H), 4.19 (t, 2H), 6.04-6.06 (m, 1H), 6.78-6.80 (m, 1H), 6.88-6.90 (m, 1H), 7.07 (bs, 1H).

9g

¹H-NMR (400 MHz, CDCl₃) δ0.86 (t, 3H), 1.15-1.45 (m, 12H), 1.6-1.75 (m, 2H), 3.06 (s, 6H), 4.23 (t, 2H), 5.95-5.98 (m, 1H), 6.17-6.20 (m, 1H), 6.79-6.80 (m, 1H).

9h

¹H-NMR (400 MHz, CDCl₃) δ0.87 (t, 3H), 1.15-1.45 (m, 12H), 1.6-1.75 (m, 2H), 3.55-3.75 (m, 8H), 4.21 (t, 2H), 5.96-6.00 (m, 1H), 6.18-6.20 (m, 1H), 6.80-6.81 (m, 1H).

9i

¹H-NMR (400 MHz, CDCl₃) σ0.92 (t, 3H), 1.2-1.5 (m, 4H), 1.7-1.9 (m, 2H), 4.33 (t, 2H), 7.18 (s, 1H), 7.3-7.4 (m, 2H), 7.79-7.81 (m, 1H), 8.48-8.49 (m, 1H), 8.80 (bs, 1H)

9k

¹H-NMR (400 MHz, CDCl₃) σ0.87 (t, 3H), 1.2-1.5 (m, 15H), 1.7-1.8 (m, 2H), 4.22 (t, 2H), 4.29 (q, 2H), 5.96-5.99 (m, 1H), 6.74-6.76 (m, 2H), 6.92-6.93 (m, 1H)

[Evaluation 9] Activities on Plants

The compounds (9a) to (9j) were evaluated by the same method as the above Evaluation 8.

The evaluation results are shown in the following Table 2.

TABLE 2

| Compound No. | Concentration (μM) | Index |
|---|---|---|
| 9a | 200 | 4 |
| 9b | 200 | 3 |
| 9c | 200 | 3 |
| 9d | 200 | 3 |
| 9e | 200 | 2 |
| 9f | 200 | 2 |
| 9g | 200 | 3 |
| 9h | 200 | 3 |
| 9i | 200 | 2 |
| 9j | 200 | 2 |

[Evaluation 10] Activities on Plants

The compound (8b), the compound (8i), and the compounds (9a) to (9f) were evaluated by the following method.

(10-1) Preparation of test emulsion

POA allyl phenyl ether (4.1 parts by weight), POE-POP glycol (1 part by weight), POE sorbitan laurate (0.8 parts by weight), glycerin (2.6 parts by weight), dimethylformamide (65.9 parts by weight), N-methylpyrrolidone (5.1 parts by weight), cyclohexanone (15.4 parts by weight), and aromatic hydrocarbon (5.1 parts by weight) were mixed and dissolved to prepare an emulsion. The compounds of the present invention (4 mg) were dissolved in this emulsion (100 μL) to prepare a test emulsion. In addition, POA means "polyoxyalkylene", POE means "polyoxyethylene", and POP means "polyoxypropylene."

(10-2) Preparation of Spray Liquid Four hundred μL of the above test emulsion was diluted with 7600 μL of water to use as a test spray liquid.

Further, 400 μL of the above test emulsion was diluted with 1600 μL of a 1% Tween20 aqueous solution to use as a spray liquid for a small amount spray test.

For a comparative spray liquid, 53 μL of a 30% pendimethalin emulsion (Gogosan emulsion: manufactured by BASF Japan) as a control pesticides was diluted with 7947 μL of water. Further, for a comparative spray liquid for a small amount spray test, 53 μL of the 30% pendimethalin emulsion was diluted with 1947 μL of water.

In addition, spray liquids which did not contain the compounds of present invention were also respectively prepared as controls of solvent.

(10-3) Spray Treatment to Stems and Leaves

A 150 cm² pot was filled with a soil, seeds of each purple amaranth, Japanese bristlegrass, southern crabgrass, and velvet leaf were sown on the surface layer, lightly covered with a soil and grown in a greenhouse. When each plant grew to a plant height of 2 to 9 cm, the test spray liquid was sprayed to the stem and leaf parts with a small spraying machine such that an active ingredient amount was 2000 g per hectare and a sprayed liquid amount was 1000 L per hectare.

Similarly, the test spray liquid for a small amount spray test was sprayed to the stem and leaf parts with a small spraying machine such that an active ingredient amount was 2000 g per hectare and a sprayed liquid amount was 250 L per hectare.

(10-4) Evaluation

Two weeks later, the above-ground grass weight in non-treated areas and the above-ground grass weight in treated areas, by the weed, were measured to calculate a killing weed rate by the following calculating formula.

(a) Calculating Formula of Weeding Rate

Killing weed rate (%)=(above-ground grass weight in non-treated area−above-ground grass weight in treated area)/(above-ground grass weight in non-treated area)×100

(b) Killing Weed Indexes

The obtained killing weed rates were evaluated, such that a killing weed index was "10" when a killing weed rate is 100%, as "9" when a killing weed rate is 99% to 90%, "8" when a killing weed rate is 89% to 80%, "7" when a killing weed rate is 79% to 70%, "6" when a killing weed rate is 69% to 60%, "5" when a killing weed rate is 59% to 50%, "4" when a killing weed rate is 49% to 40%, "3" when a killing weed rate is 39% to 30%, "2" when a killing weed rate is 29% to 20%, "1" when a killing weed rate is 19% to 10%, and "0" when a killing weed rate is 9% to 0%.

(c) Evaluation Results

The evaluation results are shown in the following Table 3.

TABLE 3

| Compound No. | Sprayed liquid amount | Purple amaranth | Japanese bristlegrass | Southern crabgrass | Velvet leaf |
|---|---|---|---|---|---|
| Leaf age (L) | | 1.5-2 | 2.5-3 | 3-3.5 | 2-2.5 |
| Plant height (cm) | | 2-4 | 5-8 | 6-8 | 8-9 |
| 8b | 1000 L/ha | 3 | 5 | 4 | 0 |
| | 250 L/ha | 8 | 5 | 2 | 6 |
| 8i | 1000 L/ha | 0 | 3 | 2 | 0 |
| | 250 L/ha | 0 | 1 | 2 | 0 |
| 9a | 250 L/ha | 8 | 3 | 2 | 3 |
| 9b | 250 L/ha | 10 | 3 | 2 | 2 |
| 9c | 1000 L/ha | 0 | 3 | 5 | 0 |
| | 250 L/ha | 1 | 2 | 3 | 5 |
| 9d | 1000 L/ha | 0 | 1 | 2 | 0 |
| | 250 L/ha | 0 | 2 | 3 | 3 |

TABLE 3-continued

| Compound No. | Sprayed liquid amount | Purple amaranth | Japanese bristlegrass | Southern crabgrass | Velvet leaf |
|---|---|---|---|---|---|
| 9e | 1000 L/ha | 0 | 2 | 2 | 0 |
|  | 250 L/ha | 0 | 2 | 2 | 2 |
| 9f | 1000 L/ha | 0 | 1 | 3 | 0 |
|  | 250 L/ha | 0 | 2 | 2 | 0 |
| pendimethalin | 1000 L/ha | 0 | — | 6 | 4 |
|  | 250 L/ha | 6 | 6 | 6 | 5 |
| Solvent control | 1000 L/ha | 0 | 0 | 1 | 0 |
|  | 250 L/ha | 0 | 0 | 0 | 1 |
| Non-treatment |  | 0 | 0 | 0 | 0 |

[Evaluation 11] Activities on Plants

The compound (8b), the compound (8f), the compound (9a), the compound (9b), the compound (9d) to the compound (9j) were evaluated by the following method.

(11-1) Preparation of Test Chemical Solution

The compound of the present invention (2 mg) was dissolved in a 1.5% Tween dimethylformamide solution (100 μL) to use as a test chemical solution.

(11-2) Seed Treatment

Eight mL of sterilized water was poured to a cherry cup (100Φ×45 mm) lined with a filter paper, subsequently 81.1 μL of the sterilized water was removed, and 81.1 μL of the test chemical solution was added such that a final concentration of the compound was 800 μM.

Further, cherry cups were similarly prepared such that a final concentration of the compound was 200 μM.

The following Table 4 shows, by the compound, amounts of the test chemical solution to be added (which is also amounts of the sterilized water to be removed).

TABLE 4

| Compound No. | 800 μM | 200 μM |
|---|---|---|
| 8b | 81.1 μL | 20.3 μL |
| 8f | 99 μL | 24.7 μL |
| 9a | — | 21.9 μL |
| 9b | — | 23 μL |
| 9d | — | 21.3 μL |
| 9e | — | 27.4 μL |
| 9f | — | 26.8 μL |
| 9g | 89.7 μL | 22.4 μL |
| 9h | 103.2 μL | 25.8 μL |
| 9i | 87.8 μL | 21.9 μL |
| 9j | 89.4 μL | 22.3 μL |

Seeds (Japanese millet: 3 grains, velvet leaf: 6 grains, Ragweed: 8 grains, morning glory: 2 grains) were planted on the filter paper in the cherry cups, followed by growing the plants in a thermostatic chamber at 25° C. under a light-dark cycle in which a light period is 12 hours and a dark period is 12 hours for 6 days.

In addition, with regards to the compound (9a) and the compound (9b), the plants were tested for 7 days.

(11-3) Evaluation

Plant growth inhibition effects of the compounds were evaluated by conversion to indexes according to the following investigation criteria.

Indexes on the Plant Growth Inhibition Effects

0: No effect

1: Growth of the stem and leave parts was inhibited 10% or more compared with non-treated area, or growth of the only root part was inhibited 20% or more compared with non-treated area.

2: Growth of the stem and leave parts was inhibited 20% or more compared with non-treated area, or growth of the only root part was inhibited 40% or more compared with non-treated area.

3: Growth of the stem and leave parts was inhibited 30% or more compared with non-treated area, or growth of the only root part was inhibited 60% or more compared with non-treated area.

4: Growth of the stem and leave parts was inhibited 40% or more compared with non-treated area, or growth of the only root part was inhibited 80% or more compared with non-treated area.

5: Growth of the stem and leave parts was inhibited 50% or more compared with non-treated area, or growth of the only root part was inhibited 100% or more compared with non-treated area.

6: Growth of the stem and leave parts was inhibited 60% or more compared with non-treated area.

7: Growth of the stem and leave parts was inhibited 70% or more compared with non-treated area.

8: Growth of the stem and leave parts was inhibited 80% or more compared with non-treated area.

9: Growth of the stem and leave parts was inhibited 90% or more compared with non-treated area.

10: Germination was inhibited.

Evaluation results are shown in Table 5.

TABLE 5

| Compound No. | Concentration (μM) | Japanese millet | Velvet leaf | Ragweed | Morning glory |
|---|---|---|---|---|---|
| 8b | 800 | 10 | 8 | 9 | 8 |
|  | 200 | 3 | 0 | 3 | 3 |
| 8f | 800 | 4 | 5 | 5 | 0 |
|  | 200 | 3 | 0 | 0 | 0 |
| 9a | 200 | 3 | 0 | 0 | 0 |
| 9b | 200 | 0 | 0 | 0 | 3 |
| 9d | 200 | 3 | 0 | 3 | 0 |
| 9e | 200 | 3 | 0 | 0 | 0 |
| 9f | 200 | 3 | 0 | 5 | 3 |
| 9g | 800 | 4 | 3 | 7 | 0 |
|  | 200 | 3 | 3 | 5 | 0 |
| 9h | 800 | 6 | 5 | 6 | 4 |
|  | 200 | 3 | 3 | 0 | 0 |
| 9i | 800 | 4 | 6 | 4 | 10 |
|  | 200 | 3 | 0 | 0 | 0 |
| 9j | 800 | 3 | 5 | 9 | 5 |
|  | 200 | 4 | 0 | 8 | 3 |

INDUSTRIAL APPLICABILITY

The plant growth inhibiting agent of the present invention does not have high toxicity to animal cells while having growth inhibiting activities on plants, due to which the agent has potential to be used as a safe pesticide and is thus industrially useful.

The invention claimed is:

1. A plant growth inhibiting agent comprising, as an active ingredient, at least one compound selected from the group consisting of a compound represented by the following formula (I') and a salt thereof:

$$(Y)_q \diagup\!\!\!\!\diagdown \text{—COR}^{3a}$$
$$| \atop \text{O—[R}^2]_n\text{—[X]}_m\text{—R}^{1a}$$

(I')

wherein
- $R^{1a}$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group;
- $R^2$ represents a substituted or unsubstituted $C_1$ to $C_{20}$ alkylene group, a substituted or unsubstituted $C_6$ to $C_{14}$ arylene group, a substituted or unsubstituted $C_3$ to $C_{13}$ heteroarylene group, or a divalent linking group consisting of a combination thereof,
- $R^{3a}$ represents OH, a substituted or unsubstituted $C_1$ to $C_6$ alkoxy group, or a group represented by a formula: $N(R^4)_2$ wherein $R^4$ represents a hydrogen atom or a substituted or unsubstituted $C_1$ to $C_6$ alkyl group, and two $R^4$ together can form a divalent organic group[)];
- X represents an oxygen atom;
- Y represents a substituent;
- q represents any integer of 0 to 3;
- n represents 0 or 1; and
- m represents 0 or 1.

2. The plant growth inhibiting agent according to claim 1, wherein the compound represented by the formula (I') is a compound represented by the following formula (I):

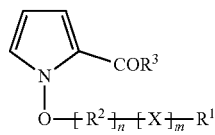

(I)

wherein
- $R^1$ represents a substituted or unsubstituted $C_1$ to $C_{20}$ alkyl group, a substituted or unsubstituted $C_6$ to $C_{14}$ aryl group, a substituted or unsubstituted $C_3$ to $C_{13}$ heteroaryl group, a substituted or unsubstituted $C_7$ to $C_{30}$ arylalkyl group, or a substituted or unsubstituted $C_4$ to $C_{30}$ heteroarylalkyl group;
- $R^2$ represents a substituted or unsubstituted $C_1$ to $C_{20}$ alkylene group, a substituted or unsubstituted $C_6$ to $C_{14}$ arylene group, a substituted or unsubstituted $C_3$ to $C_{13}$ heteroarylene group, or a divalent linking group consisting of a combination thereof;
- $R^3$ represents OH or NH;
- X represents an oxygen atom;
- n represents 0 or 1; and
- m represents 0 or 1.

3. The plant growth inhibiting agent according to claim 2, wherein in the formula (I), $R^3$ represents OH.

4. The plant growth inhibiting agent according to claim 2, wherein in the formula (I), $R^1$ represents a substituted or unsubstituted $C_1$ to $C_{20}$ alkyl group, a substituted or unsubstituted $C_6$ to $C_{14}$ aryl group, or a substituted or unsubstituted $C_7$ to $C_{30}$ arylalkyl group.

5. The plant growth inhibiting agent according to claim 2, wherein in the formula (I), $R^1$ is a substituted or unsubstituted $C_1$ to $C_{20}$ alkyl group, or a substituted or unsubstituted $C_7$ to $C_{30}$ arylalkyl group, and $R^3$ represents OH.

6. The plant growth inhibiting agent according to claim 2, wherein in the formula (I), n represents 0, and m represents 0.

7. The plant growth inhibiting agent according to claim 6, wherein in the formula (I), $R^1$ represents a $C_1$ to $C_4$ alkyl group, or a benzyl group.

8. A compound represented by the following formula (III), or a salt thereof:

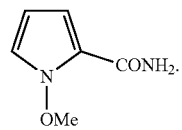

(III)

* * * * *